United States Patent [19]

Delaney et al.

[11] Patent Number: 5,414,013
[45] Date of Patent: May 9, 1995

[54] TRIFLUOROMETHYL MERCAPTAN AND MERCAPTOACYL DERIVATIVES AND METHOD OF USING SAME

[75] Inventors: Norma G. Delaney, Princeton; George C. Rovnyak, Hopewell, both of N.J.; Melanie J. Loots, Champaign, Ill.

[73] Assignee: E. R. Squibb & Sons, Inc., Princeton, N.J.

[21] Appl. No.: 38,032

[22] Filed: Mar. 26, 1993

Related U.S. Application Data

[60] Division of Ser. No. 690,436, Apr. 24, 1991, Pat. No. 5,223,516, which is a continuation-in-part of Ser. No. 497,386, Mar. 22, 1990, abandoned.

[51] Int. Cl.$^6$ ............... A61K 31/40; C07D 207/06; C07D 207/08
[52] U.S. Cl. ............... 514/423; 548/433; 548/435
[58] Field of Search ............... 548/533, 535; 514/423

[56] References Cited

U.S. PATENT DOCUMENTS

| | | | |
|---|---|---|---|
| 4,216,160 | 8/1980 | Dorn et al. | 260/455 R |
| 4,241,076 | 12/1980 | Ondetti et al. | 424/274 |
| 4,333,943 | 6/1982 | Kurchacova et al. | 548/253 |
| 4,513,009 | 4/1985 | Roques et al. | 514/513 |
| 4,690,936 | 9/1987 | Ryan et al. | 514/362 |
| 4,692,458 | 9/1987 | Ryan et al. | 514/362 |
| 4,734,420 | 3/1988 | Ryan et al. | 514/362 |
| 4,774,256 | 9/1988 | Delaney et al. | 514/513 |
| 4,833,152 | 5/1989 | Ryan et al. | 514/362 |
| 4,874,792 | 10/1989 | Gleason et al. | 548/252 |
| 4,879,309 | 11/1989 | Doll et al. | 514/513 |
| 5,093,361 | 5/1992 | Reiner et al. | 558/254 |
| 5,136,076 | 8/1992 | Duhamel et al. | 558/254 |
| 5,166,390 | 11/1992 | Weinstein et al. | 558/254 |

FOREIGN PATENT DOCUMENTS

| | | |
|---|---|---|
| 890948 | 10/1981 | Belgium . |
| 115997 | 8/1984 | European Pat. Off. . |
| 159254 | 10/1985 | European Pat. Off. . |
| 318377 | 5/1989 | European Pat. Off. . |
| 318859 | 6/1989 | European Pat. Off. . |
| 361365 | 4/1990 | European Pat. Off. . |
| 84/0670 | 1/1984 | South Africa . |

OTHER PUBLICATIONS

Wilkerson, "Antihypertensive Thioester Compounds", 2244 Research Disclosure (1986) Jun. No. 266.

*Primary Examiner*—C. Warren Ivy
*Assistant Examiner*—Raymond Covington
*Attorney, Agent, or Firm*—Stephen B. Davis

[57] ABSTRACT

Compounds of the formula $$R_3-S-CH_2-CH\underset{\underset{O}{\|}}{\overset{\overset{CF_3}{|}}{\underset{|}{(CH_2)_m}}}-C-NH-\overset{\overset{R_1}{|}}{C}H-\overset{\overset{O}{\|}}{C}-Z$$

wherein Z is $$-NH-\overset{\overset{R_8}{|}}{C}H-COR_2,$$

proline, pipecolic acid, an indolecarboxylic acid or an isoquinolinecarboxylic acid. These compounds are useful as cardiovascular agents.

5 Claims, No Drawings

TRIFLUOROMETHYL MERCAPTAN AND MERCAPTOACYL DERIVATIVES AND METHOD OF USING SAME

RELATED APPLICATION

This application is a division of Ser. No. 690,436 filed Apr. 24, 1991, now U.S. Pat. No. 5,233,516, which is a continuation-in-part of Ser. No. 497,386 filed Mar. 22, 1990, now abandoned.

SUMMARY OF THE INVENTION

In accordance with the present invention, novel neutral endopeptidase inhibitors and methods for their use are disclosed. Compounds of the present invention, useful, for example, as cardiovascular agents, have the general formula

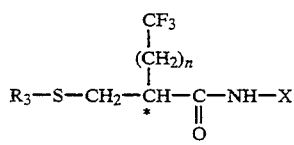

I wherein X is

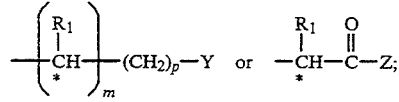

Y can be —$COR_2$,

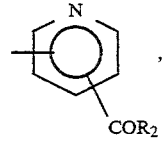

phenyl, phenyl substituted with alkyl of 1 to 4 carbons, alkoxy of 1 to 4 carbons, alkylthio of 1 to 4 carbons, hydroxy, halo, nitro or trifluoromethyl, or a heterocyclic group selected from thiazolyl, 4,5-dihydrothiazolyl, pyridyl, oxazolyl, isoxazolyl, imidazolyl, tetrazolyl, benzimidazole, benzothiazolyl or benzoxazolyl including substituted heterocyclic groups wherein the substituents are selected from halo, alkyl and phenyl;

Z can be

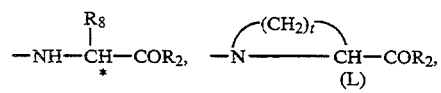

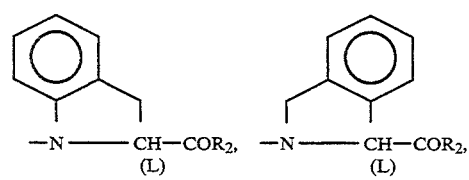

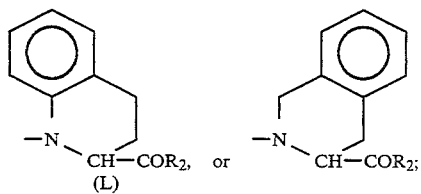

m is zero or 1;
n is zero, 1 or 2;
p is zero or 1 to 6;
t is 2, 3 or 4;
with the proviso that m and p are both zero when Y is

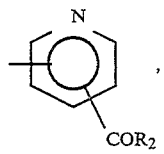

and with the proviso that m and p are not both zero when Y is —$COR_2$;

$R_1$ and $R_8$ are independently hydrogen, lower alkyl, halo substituted lower alkyl,

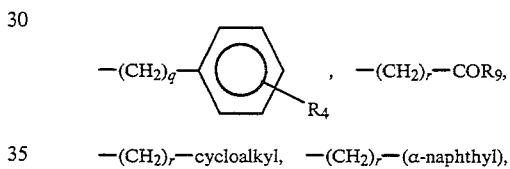

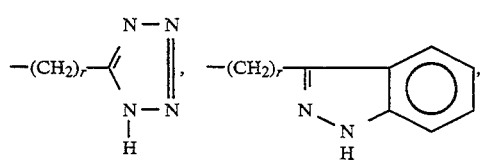

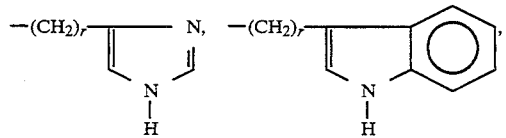

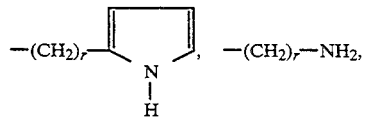

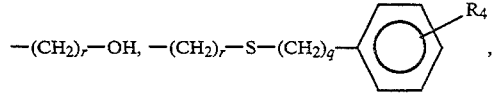

—$(CH_2)_r$—O—lower alkyl,

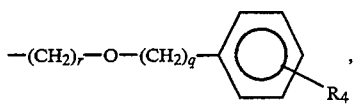,

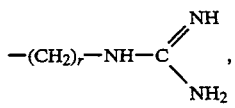, or

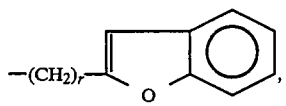, $R_2$ and $R_9$ are independently hydroxy, lower alkoxy, (phenyl)lower alkoxy,

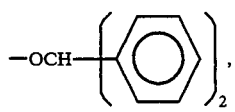,

—O⊖M⊕ where M⁺ is a salt forming metal ion,

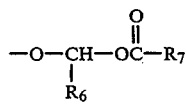

or —NRR' where R and R' are independently selected from hydrogen, alkyl and

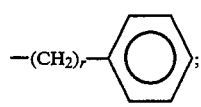;

$R_3$ is hydrogen,

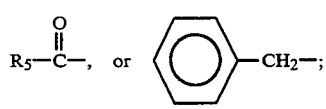;

$R_4$ is hydrogen, lower alkyl of 1 to 4 carbons, lower alkoxy of 1 to 4 carbons, lower alkylthio of 1 to 4 carbons, halo, hydroxy, $CF_3$, phenyl,

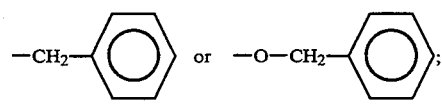;

$R_5$ is lower alkyl,

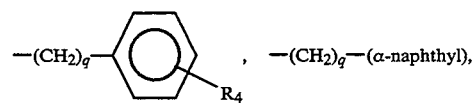,

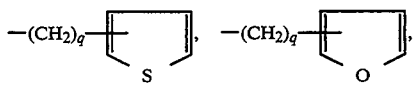,

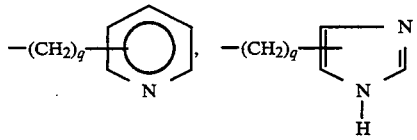

or

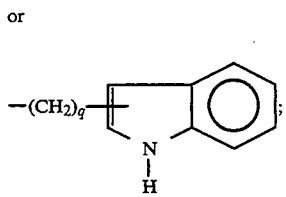;

$R_6$ is hydrogen, lower alkyl, cycloalkyl or phenyl;
$R_7$ is hydrogen, lower alkyl, lower alkoxy or phenyl;
r is an integer from 1 to 4; and,
q is zero or an integer from 1 to 7.

DETAILED DESCRIPTION OF THE INVENTION

This invention in its broadest aspects relates to neutral endopeptidase inhibitors of formula I and to the methods of treating congestive heart failure, lowering blood pressure and producing diuresis and natriuresis by administering a pharmaceutical composition containing same. Unexpectedly, the trifluoromethyl substituent compounds of formula I have been found to be significantly more active as neutral endopeptidase inhibitors than mercaptan and mercaptoalkanoyl compounds not having the trifluoromethyl moiety.

The term lower alkyl used in defining various symbols refers to straight or branched chain radicals having up to seven carbons unless specifically stated otherwise. The preferred lower alkyl groups are straight or branched chain of up to four carbons. Similarly the terms lower alkoxy and lower alkylthio refer to such lower alkyl groups attached to an oxygen or sulfur.

The term cycloalkyl refers to saturated rings of 4 to 7 carbon atoms with cyclopentyl and cyclohexyl being most preferred.

The term halogen refers to chloro, bromo, fluoro and iodo.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

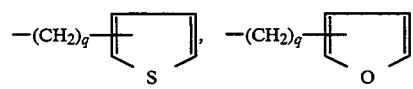

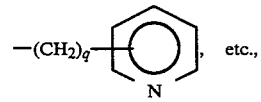, etc., represent that the alkylene bridge is attached to an available carbon atom.

The compounds of formula I can be prepared by coupling a carboxylic acid of the formula

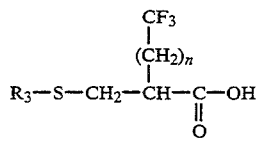

to the amino intermediate of the formula $$H_2N-X \qquad (III)$$

The intermediate of formula III can be employed as the free base or as the hydrochloride salt. The carboxylic acid of formula II is preferably converted to an activated form such as an acid chloride, mixed anhydride, etc.

Preferably, the amino intermediate of formula III is first treated with bis(trimethylsilyl)trifluoroacetamide or bis(trimethylsilyl)acetamide in an aprotic solvent such as tetrahydrofuran or acetonitrile followed by addition of compound II as the acid chloride.

The above coupling step can also be carried out using the protected form of compound II, that is,

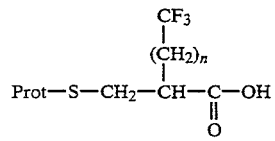

where Prot is a protecting group, e.g., p-methoxybenzyl. Subsequent deprotection can be accomplished by known methods, such as those described in U.S. Pat. No. 4,311,697 by Krapcho.

Alternatively, the reaction is preferably carried out in the presence of an organic base, e.g. triethylamine. Two equivalents of the amino intermediate III may be employed as both reactant and base.

For those cases wherein amino intermediate III does not contain a free carboxylic acid, reaction of acid II and amine III can also be effected with a water soluble carbodiimide reagent such as [1-(3-dimethylaminopropyl)-3-ethylcarbodiimide hydrochloride].

The resulting products, wherein X contains a —COR$_2$ moiety which is an ester, can be hydrolyzed by treating with a base such as sodium hydroxide to provide compounds where R$_2$ is hydroxy and R$_3$ is hydrogen, since concomitant hydrolysis of an existing acylthio group

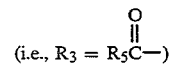

also occurs.

The S-acyl derivatives of formula I

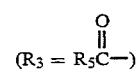

can be treated with a base, such as ammonium hydroxide, hydroxylamine, sodium hydroxide and the like, to provide mercaptan derivatives (i.e., compounds of formula I where R$_3$=H) by known techniques.

Of course, the mercaptan products of formula I, i.e., where R$_3$ is hydrogen, can be acylated with an acid chloride of the formula

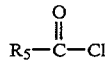

to introduce other acyl groups.

The acylthio carboxylic acids of formula II are described in various literature and patent references. For example, such carboxylic acids wherein n=0 are described by Ondetti et al. in U.S. Pat. No. 4,154,935.

Protected thiocarboxylic acids of formula II' are prepared using methods described by Krapcho in U.S. Pat. No. 4,311,097.

Compounds of formula II where n is other than zero and R$_3$ is

may be prepared by alkylation of a malonic ester with a compound of formula V, where L' represents a leaving group such as iodo or trifluoromethanesulfonyloxy, $$CF_3(CH_2)_n-L', \qquad (V)$$

using a base such as sodium hydride or potassium hexamethyldisilylazide in an aprotic solvent such as tetrahydrofuran or dimethylformamide to give a substituted malonic ester of the formula $$CF_3(CH_2)_n-CH(CO_2CH_3)_2. \qquad (VI)$$

Saponification of the malonic esters of formula VI and Mannich reaction with dimethylamine and formaldehyde gives acrylic acids of formula

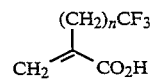

which are reacted with a thio acid to give compounds of formula II where n is other than zero and R$_3 \neq$H. Reaction of compounds of formula II as described above provides the S-acyl and mercaptan derivatives of formula I where n is other than zero. Alternatively, intermediates of formula II where n is other than zero may also be prepared by condensation of an aldehyde of formula $$CF_3(CH_2)_{n-1}-CHO \qquad (VIII)$$

with malonic acid in the presence of acetyl chloride to give compounds of formula

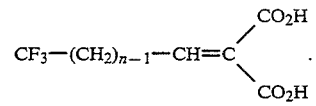

Catalytic hydrogenation over palladium/carbon and Mannich reaction and thio acid addition as described above affords the corresponding compounds of formula II.

Additionally, intermediates of formula II where n is other than zero and $R_3$ is benzyl may be prepared by alkylation of an acid of the formula

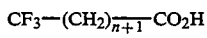   X with benzyl bromomethylthioether to give compounds of formula II wherein $R_3$ is benzyl.

In the above reactions if $R_1$ or $R_5$ is

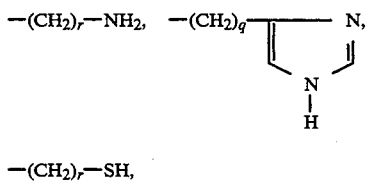

then the amino, imidazolyl, mercaptan or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by treatment with acid or other known methods following completion of the reaction.

The ester products of formula I wherein $R_2$ is

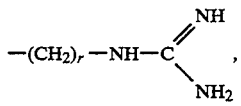

can be obtained by treating the product of formula I wherein $R_2$ is hydroxy with a molar equivalent of a compound of the formula

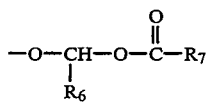   XI wherein L is a leaving group such as chlorine, bromine, toluenesulfonyloxy, etc., in the presence of a base, such as triethylamine or potassium carbonate, in a polar solvent such as dimethylformamide.

Preferred compounds of this invention are those of formula I wherein

X is

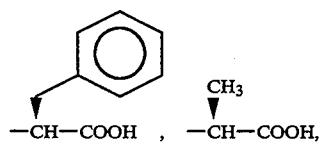

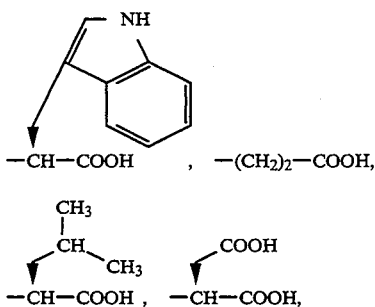

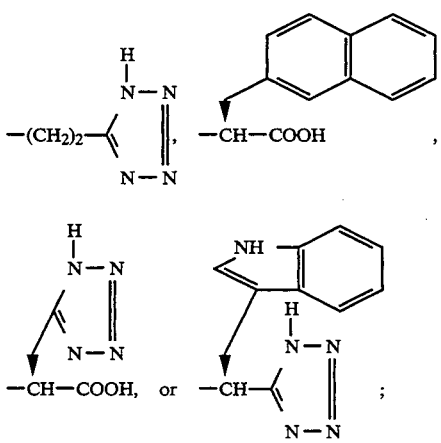

$R_3$ is hydrogen,

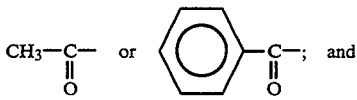

n is zero or one, especially zero.

The compounds of formula I wherein $R_2$ is hydroxy form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts, such as calcium or magnesium, and salts derived from amino acids, such as arginine, lysine, etc. The salts are obtained by reacting the acid form of the compound with an equivalent of the base supplying the desired ion in a medium in which the salt precipitates or in aqueous medium and then lyophilizing.

As shown above, the compounds of formula I wherein $R_1$ or $R_8$ is other than hydrogen contain asymmetric centers as represented by the * in formula I. An additional asymmetric center is present in the ester products when $R_6$ is other than hydrogen. Thus, the compounds of formula I can exist in enantiomeric or diastereomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I inhibit the activity of neutral endopeptidase (EC 3.4.24.11), a membrane-bound zinc metallopeptidase found in many tissues including the brain and kidney. Neutral endopeptidase hydrolyzes peptide bonds which are on the amino terminal side of hydrophobic amino acid residues.

While not limiting the scope of this invention to a specific theory or mechanism of action, inhibition of neutral endopeptidase is believed to result in reduced inactivation of exogenously administered or endogenous atrial natriuretic peptides. Thus, the compounds of formula I are useful in the treatment of hypertension, congestive heart failure, renal failure or hepatic cirrhosis. Diuresis, natriuresis, and blood pressure reduction are produced in a mammalian host such as man by the administration of from about 1 mg to about 100 mg per kg of body weight per day, preferably from about 1 mg to about 50 mg per kg of body weight per day, of one or more neutral endopeptidase inhibitors of formula I or a pharmaceutically acceptable salt thereof. The neutral endopeptidase inhibitors of formula I are preferably administered orally, but parenteral routes such as subcutaneous, intramuscular, and intravenous can also be employed. The daily dose can be administered singly or can be divided into two to four doses administered throughout the day.

The neutral endopeptidase inhibitors of formula I can also be administered in combination with other blood pressure lowering agents. For example, the neutral endopeptidase inhibitors of formula I can be combined for dual administration with an angiotensin converting enzyme (ACE) inhibitor such as captopril, zofenopril, fosinopril, enalapril, lisinopril, etc. Such combination would be at a weight ratio of endopeptidase inhibitor to ACE inhibitor of from about 1:10 to about 10:1.

The neutral endopeptidase inhibitors of formula I can also be administered in combination with human ANF 99-126. Such combination would contain the inhibitor of formula I at from about 1 to about 100 mg per kg of body weight and the human ANF 99-126 at from about 0.001 to about 0.1 mg per kg of body weight.

The neutral endopeptidase inhibitors of formula I or pharmaceutically acceptable salts thereof can also be administered to a mammalian host such as man to inhibit the degradation of endogenous opioid pentapeptides, [Met$^5$]-enkephalin (Tyr-Gly-Gly-Phe-Met) and [Leu$^5$]-enkephalin (Tyr-Gly-Gly-Phe-Leu), in the brain or in peripheral tissues.

For this reason the compounds of the invention are useful in therapeutic areas including for example the treatment of asthma, inflammation, pain, epilepsy, affectlye disorders, dementia and geriatric confusion, obesity and gastrointestinal disorders (especially diarrhea and irritable bowel syndrome), the modulation of gastric acid secretion and the treatment of hyperreninaemia and leukemia. As such, the compounds of this invention, and pharmaceutically acceptable salts thereof, can be administered to patients orally or parenterally in an effective amount within the daily dosage range of from about 0.1 to about 25 mg of compound per kg of patient body weight. Administration can be once daily or in 2 to 4 divided daily doses.

Additionally, the compounds of formula I wherein X is

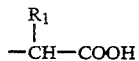

also possess angiotensin converting enzyme inhibition activity. Thus, these compounds of formula I are dual inhibitors and can be employed in therapeutic areas in which angiotensin converting enzyme inhibitors such as captopril have been reported to be useful. These areas include cardiovascular uses such as treating hypertension, congestive heart failure, reducing pre- and postischemic myocardial arrhythmias and fibrillation, etc., as well as improving cognitive function, treating depression and anxiety, etc.

The inhibitors of formula I and other pharmaceutically acceptable ingredients can be formulated for the above described pharmaceutical uses. Suitable compositions for oral administration include tablets, capsules and elixirs, and suitable compositions for parenteral administration include sterile solutions and suspensions. About 10 to 50 mg of active ingredient is compounded with physiologically acceptable vehicle, carrier, excipient, binder, preservative, stabilizer, flavoring, etc., in a unit dose form as called for by accepted pharmaceutical practice.

The following examples are illustrative of the invention. Temperatures are given in degrees centigrade.

EXAMPLE 1

1-[3,3,3-Trifluoro-2-(mercaptomethyl)-1-oxopropyl]-L-phenylalanine

A.

N-[2-[(Acetylthio)methyl]-3,3,3-trifluoro-1-oxopropyl]-L-phenylalanine

Phenylalanine (0.825 g, 5 mmol) was suspended in 10 mL of methylene chloride, bis(trimethylsilyl) trifluoroacetamide (4 mL) was added, and the mixture was stirred at room temperature for 3 hours. An additional 4 mL of bis(trimethylsilyl)trifluoroacetamide was added and the mixture stirred overnight. Another 4 mL of bis(trimethylsilyl) trifluoroacetamide was added, followed by 5 mL dimethylformamide. All solid dissolved over 3 hours to give a clear solution, which was cooled to 5° C. 2-Trifluoro-methyl-3-acetylthiopropionyl chloride (0.99 g, 4.22 mmol) in 2 mL of tetrahydrofuran was added dropwise and the mixture stirred overnight at room temperature. The reaction mixture was concentrated on the rotary evaporator. Water (20 mL) was added to the residue and this mixture was stirred for 15 minutes and then partitioned between ethyl acetate and 5 percent potassium hydrogen sulfate. The ethyl acetate solution was washed with brine and concentrated to an oil. This oil was chromatographed on 400 mL of Merck silica gel, using 40:1:1 methylene chloride: methanol:acetic acid as eluant to give the title A compound as an oil (0.94 g, 2.6 mmol). TLC R$_f$=0.60 (20:1:1 methylene chloride:methanol:acetic acid).

B.

1-[3,3,3-Trifluoro-2-(mercaptomethyl)-1-oxopropyl]-L-phenylalanine

The title A compound (890 mg, 2.45 mmol) was stirred at 0° under argon with 1.6 mL of concentrated ammonium hydroxide and 3.5 mL water for 5 minutes, after which 100 mL of 5 percent potassium hydrogen sulfate was added, and the resulting solution extracted with ethyl acetate. The combined ethyl acetate extract was washed with brine, dried over sodium sulfate and concentrated to a yellow oil, which was then chromatographed on 300 mL of Merck silica, using 40:1:1 methylene chloride:methanol:acetic acid as eluant to give the title mixture of diastereomers as a white solid (120 mg), m.p. 99° C. TLC $R_f$=0.64 (20:1:1 methylene chloride:-methanol:acetic acid), $[\alpha]_D$= +18.6° (c=0.5, methanol).

Analysis calc'd for $C_{13}H_{14}F_3NO_3S\cdot 0.65\ H_2O$: C, 46.89; H, 4.63; N, 4.21; F, 17.11; S, 9.63; SH, 9.92; Found: C, 46.56; H, 4.39; N, 4.19; F, 17.50; S, 9.61; SH, 10.18.

EXAMPLE 2

1-[3,3,3-Trifluoro-2-(mercaptomethyl)-1-oxopropyl]-L-alanine

A.

N-[2-[(Acetylthio)methyl]-3,3,3-trifluoro-1-oxopropyl]-L-alanine

Alanine (445 mg, 5 mmol) was suspended in 5 mL of methylene chloride, bis (trimethylsilyl) trifluoroacetamide (4 mL) was added, and the resulting solution was stirred for 3 hours at room temperature. Dimethylformamide (4 mL) was added, and the mixture stirred overnight. All material went into solution. 2-Trifluoromethyl-3-acetylthio propionyl chloride (1 g, 4.26 mmol) in 2 mL of tetrahydrofuran was added, and the mixture was stirred overnight at room temperature. The reaction mixture was concentrated on the rotary evaporator. The residue was then partitioned between ethyl acetate and 5 percent potassium hydrogen sulfate. The ethyl acetate solution was washed with 5 percent potassium hydrogen sulfate and brine, and concentrated to a light brown oil. This oil was chromatographed on 400 mL of Merck silica gel, using 40:1:1 methylene chloride:methanol:acetic acid as eluant, to give the title A compound as a yellow oil (960 mg). TLC $R_f$=0.45 (20:1:1 methylene chloride:methanol: acetic acid).

B.

1-[3,3,3-Trifluoro-2-(mercaptomethyl)-1-oxo-propyl]-L-alanine

The title A compound (960 mg, 3.3 mmol) was stirred at 0° C. under argon with 2.2 mL of concentrated ammonium hydroxide and 4.7 mL of water for 10 minutes, and then 5% potassium hydrogen sulfate (100 mL) was added. The resulting solution was extracted with ethyl acetate. The combined ethyl acetate extract was washed with 5% potassium hydrogen sulfate and brine, dried over magnesium sulfate and concentrated to an oil, which was then chromatographed on 200 mL of Merck silica gel, using 40:1:1 methylene chloride:methanol:acetic acid as eluant, to give the title mixture of diastereomers as a white solid (720 mg), m.p. 106°-107° C., TLC $R_f$=0.40 (20:1:1 methylene chloride: methanol:acetic acid), $[\alpha]_D$= -27.1° (c=0.73, methanol).

Analysis calc'd for $C_7H_{10}F_3NO_3S$: C, 34.28; H, 4.11; N, 5.71; F, 23.24; S, 13.07; SH, 13.49; Found: C, 34.52; H, 4.25; N, 5.76; F, 23.20; S, 12.76; SH, 13.74.

EXAMPLE 3

N-[2-[(Acetylthio)methyl]-3,3,3-trifluoro-1-oxopropyl]-L-phenylalanine, isomer A A stirred suspension of L-phenylalanine (7.60 g, 46 mmol) in 45 mL of dry acetonitrile under argon was cooled to 0° C. and bis(trimethylsilyl)trifluoroacetamide (24.7 mL, 92 mmol) was added. The reaction mixture was allowed to stir and slowly warm to room temperature. After 4 hours, practically all of the amino acid was in the solution, which was light yellow in color. 2-Trifluoromethyl-3-acetylthio propionyl chloride (4.69 g, 20 mmol), dissolved in 10 mL of acetonitrile, was added dropwise over a period of about 45 minutes at 5° C. and thereafter the reaction mixture was allowed to warm to room temperature and stir overnight. The mixture was evaporated under reduced pressure to give a light yellow oil. The oil was partitioned between water (75 mL) and ethyl acetate (100 mL). The entire mixture was filtered to remove a white precipitate (phenylalanine), and the organic layer was separated. The aqueous phase was extracted once more with 50 mL of ethyl acetate. The combined ethyl acetate extract was washed with brine, dried over anhydrous magnesium sulfate and evaporated to give 20.1 g of the crude mixture of diastereomers as a light yellow solid. A 2.0 g portion of the product was flash chromatographed on silica gel (125:1 silica gel to compound), using ethyl acetate: hexanes:acetic acid, 100:100:1 as the eluent, to yield 0.370 g of the faster eluting diastereomer (isomer A) and 0.383 g of the slower eluting diastereomer (isomer B). The remaining 18.1 g of crude material was flash chromatographed similarly to yield 2.67 g of isomer A and 2.92 g of isomer B. The combined yield of isomer A was 3.04 g as a white crystalline solid, m.p. 183°-185° C., TLC $R_f$=0.30 (200:100:1 ethyl acetate:-hexanes:acetic acid), $[\alpha]_D$= -98.8° (c=1.00, methanol).

Analysis calc'd for $C_{15}H_{16}F_3NO_4S$: C, 49.58; H, 4.44; N, 3.86; F, 15.69; S, 8.82; Found: C, 49.63; H, 4.35; N, 3.70; F, 15.35; S, 8.81.

EXAMPLE 4

N-[2-[(Acetylthio)methyl]-3,3,3-trifluoro-1-oxopropyl]-L-phenylalanine, isomer B The crude mixture of diastereomers of Example 3 (20.1 g) was flash chromatographed on silica gel (125:1 silica gel to compound) using ethyl acetate:hexanes:acetic acid (100:100:1) as the eluent to give the slower eluting isomer (isomer B): 0.38 g and 2.92 g. The 2.92 g portion was triturated with hexanes containing 10 percent ethyl acetate, and the white crystalline solid was filtered to give 0.72 g of material. The filtrate was concentrated to give 2.1 g of material which was flash chromatographed as described above to give approximately 1.3 g of material which was combined with the 0.38 g and 0.72 g portions and evaporated from methanol to yield 2.20 g of the title isomer B compound as a white crystalline solid, m.p. 134°-136° C., TLC $R_f$=0.14 (200:100:1 ethyl acetate:hexanes:acetic acid), $[\alpha]_D$= +118° (c=1.00, methanol).

Analysis calc'd for $C_{15}H_{16}F_3NO_4S$: C, 49.58; H, 4.44; N, 3.86; F, 15.69; S, 8.82; Found: C, 49.58; H, 4.33; N, 3.78; F, 15.44; S, 8.54.

Examples 5 and 6 describe the preparation of the single diastereomers, isomers A and B, corresponding to the mixture of diastereomers of Example 1.

EXAMPLE 5

N-[3,3,3-Trifluoro-2-(mercaptomethyl)-1-oxopropyl]-L-phenylalanine, isomer A A suspension of the title isomer A compound from Example 3 (500 mg, 1.37 mmol) in 0.9 mL of concentrated ammonium hydroxide and 2 mL of water was stirred at room temperature under argon for 5-6 minutes, during which time a clear solution resulted. The solution was treated with 50 mL of 5 percent potassium hydrogen sulfate solution and the resulting aqueous solution was extracted with four 25 mL portions of ethyl acetate. The combined ethyl acetate extract was dried over anhydrous magnesium sulfate and evaporated to afford 0.43 g of crude product. Flash chromatography over silica gel (125:1 silica gel to compound) with $CH_2Cl_2:CH_3OH:HOAc$, 40:1:1 gave 370 mg of product. Similarly, another 2.30 g (6.3 mmol) of the title isomer A compound from Example 3 was deacylated, and purification by flash chromatography yielded 2.00 g of product. The two products were combined and the resulting solid was triturated with hexanes and a few drops of ether. The solvent was decanted off and the solid dried in vacuo to give 1.79 g of the title compound as a white crystalline solid, m.p. 133°–134.5° C., TLC $R_f$=0.30 (40:1:1 methylene chloride:methanol:acetic acid), $[\alpha]_D$=−8.1° (c=1.00, methanol).

Analysis calc'd for $C_{13}H_{14}F_3NO_3S$: C, 48.59; H, 4.39; N, 4.36; F, 17.74; S, 9.98; SH, 10.29; Found: C, 48.47; H, 4.26; N, 4.30; F, 17.49; S, 10.34; SH, 10.57.

EXAMPLE 6

N-[3,3,3-Trifluoro-2-(mercaptomethyl)-1-oxopropyl]-L-phenylalanine, isomer B

A suspension of the title isomer B compound of Example 4 (2.05 g, 5.64 mmol) in 3.6 mL of concentrated ammonium hydroxide and 8.0 mL of water was stirred under argon for 7–10 minutes. The clear light yellow solution was acidified with aqueous 5 percent potassium hydrogen sulfate solution to pH 2 and extracted with four 50 mL portions of ethyl acetate. The combined organic extract was washed with 50 mL of brine, dried over anhydrous magnesium sulfate and the solvent removed under reduced pressure to afford 1.87 g of yellow solid. Flash chromatographic purification of the crude product over silica gel (130:1 silica gel to compound) using $CH_2Cl_2:CH_3OH: HOAc$, 50:1:1 as eluent gave 1.70 g of the title compound as a white solid, m.p. 148°–150° C., TLC $R_f$=0.29 (40:1:1 methylene chloride:methanol:acetic acid), $[\alpha]_D$= +49.2° (c=1.00, methanol).

Analysis calc'd for $C_{13}H_{14}F_3NO_3S$: C, 48,59; H, 4.39; N, 4.36; F, 17.74; S, 9.98; SH, 10.29; Found: C, 48.43; H, 4.10; N, 4.21; F, 17.42; S, 10.27; SH, 10.09.

EXAMPLE 7

N-[2-[(Acetylthio)methyl]-3,3,3-trifluoro-1-oxopropyl]-L-tryptophan, isomer A

A stirred suspension of L-tryptophan (4.08 g., 20 mmol.) in 50 mL of dry acetonitrile under argon was cooled to 0°–5° C. and bis(trimethylsilyl)trifluoroacetamide (5.3 mL, 20 mmol.) was added. The reaction mixture was allowed to stir and warm to room temperature. After 3 hours, the solution was cooled to 5° C. and a solution of 2-trifluoromethyl-3-acetylthiopropionyl chloride (4.69 g., 20 mmol) in 7 mL of acetonitrile was gradually added over 45 minutes. The reaction mixture was allowed to stir overnight, gradually warming to room temperature. The solvent was evaporated and the yellow oily residue was partitioned between ethyl acetate (50 mL) and water (35 mL). The aqueous phase was further extracted with ethyl acetate (3×50 mL), and the combined ethyl acetate extract was washed with brine, dried (MgSO4) and evaporated to 14.15 g. of a yellow oily residue. A 12.25 g. portion of the product was flash chromatographed on silica gel (120:1 silica gel to compound) using ethyl acetate: hexanes:acetic acid, 150:100:1 to give 1.9 g. of the faster eluting diastereomer (isomer A), 4.2 g. of both diastereomers, and 1.5 g. of the slower eluting diastereomer (isomer B). Further elution with ethyl acetate:hexanes:acetic acid, 200:100:1 gave an additional 170 mg. of isomer B. The mixed fractions were rechromatographed using the same conditions to give 1.65 g. of isomer A and 1.76 g. of isomer B. The 1.9 g. and 1.65 g. portions of isomer A were combined and recrystallized from toluene to give 2.8 g. of off-white crystalline solid. An additional 360 mg. of isomer A (from flash chromatography of 1.5 g. of the crude product) was recrystallized from toluene to give 260 mg. of white crystalline solid; the total yield of title isomer A compound was 3.06 g.; m.p. 140°–143° C., TLC $R_f$=0.46 (300:100:1 ethyl acetate:hexanes: acetic acid), $[\alpha]_D$=96.0° (c=1.00, methanol).

Analysis calc'd for $C_{17}H_{17}F_3N_2O_4S$: C, 50.74; H, 4.26; N, 6.96; F, 14.16; S, 7.97; Found: C, 50.47; H, 4.04; N, 6.86; F, 13.82; S, 8.18.

EXAMPLE 8

N-[2-[(Acetylthio)methyl]-3,3,3-trifluoro-1-oxopropyl]-L-tryptophan, isomer B

Combined isomer B from Example 7 (3.62 g.) was recrystallized from toluene to give 2.56 of title isomer B compound as a powdery white solid; m.p. 148°–151° C., TLC $R_f$=0.35 (300:100:1 ethyl acetate:hexanes:acetic acid), $[\alpha]_D$= +110.6° (c=1.00, methanol).

Analysis calc'd for $C_{17}H_{17}F_3N_2O_4S \cdot 0.1$ $H_2O$: C, 50.51; H, 4.29; N, 6.93; F, 14.10 S, 7.93 Found: C, 50.67; H, 4.08; N, 6.62; F, 13.72; S, 7.82.

EXAMPLE 9

N-[3,3,3-trifluoro-2-(mercaptomethyl)-1-oxopropyl]-L-tryptophan, isomer A

A suspension of the product of Example 7 (2.6 g., 6.5 mmol.) in 4.25 mL of concentrated ammonium hydroxide and 9.3 mL of water was stirred at room temperature under argon for 12–15 minutes. The resulting solution was acidified with 200 mL of 5% potassium hydrogen sulfate and extracted with ethyl acetate (5×50 mL). The combined ethyl acetate extract was washed with brine, dried (MgSO4) and evaporated to give 2.4 g. of a light yellow solid. This material was combined with an additional 80 mg. of compound and flash chromatographed on 300 g. of silica gel eluting with methylene chloride:methanol:acetic acid, 40:1:1 to give 2.3 g. of white solid. This solid was triturated with toluene containing approximately 5% ethyl acetate, and 1.25 g. of white crystalline solid was collected by filtration. The filtrate was evaporated to dryness and the residue was triturated in a similar fashion to produce an additional 560 mg. of material which was combined with the initial 1.25 g. crop to yield 1.81 g. of title isomer A compound as a white crystalline solid; m.p. 148.5°–150.5° C., TLC $R_f$=0.48 (300:100:1 ethyl acetate:hexanes:acetic acid), $[\alpha]_D$=−10.3° (c=1.00, methanol).

Analysis calc'd for $C_{15}H_{15}F_3N_2O_3S$: C, 49.99; H, 4.20; N, 7.78; F, 15.82; S, 8.90; SH, 9.18; Found: C, 49.98; H, 3.96; N, 7.54; F, 15.42; S, 9.12; SH, 9.38.

EXAMPLE 10

N-[3,3,3-trifluoro-2-(mercaptomethyl)-1-oxopropyl]-L-tryptophan, isomer B

A suspension of the product from Example 8 (2.41 g., 5.99 mmol) in 3.75 mL of concentrated ammonium hydroxide and 8.25 mL of water was stirred at room temperature under argon for 12–15 minutes. The resulting solution was acidified with 200 mL of 5% potassium hydrogen sulfate and extracted with ethyl acetate (5×50mL). The combined ethyl acetate extract was washed with brine, dried (MgSO$_4$) and evaporated to give 2.3 g. of a yellow gummy solid. Flash chromatography on 315 g. of silica gel eluting with methylene chloride:methanol:acetic acid, 40:1:1 gave 2.1 g. of a light yellow, glassy residue which was triturated with toluene containing approximately 5% ethyl acetate to give 1.55 g. of title isomer B compound as a white crystalline solid, m.p. 144°–147° C., TLC R$_f$=0.44 (300:100:1 ethyl acetate:hexanes:acetic acid), [α]$_D$=+35.8° (c=1.00, methanol).

Analysis calc'd for C$_{15}$H$_{15}$F$_3$N$_2$O$_3$S·0.1 H$_2$O: C, 49.74; H, 4.23; N, 7.74; F, 15.74; S, 8.85; SH, 9.13; Found: C, 50.04; H, 3.99; N, 7.45; F, 15.36; S, 9.08; SH, 9.34.

EXAMPLE 11

3-[[2-[(Acetylthio)methyl]-3,3,3-trifluoro-1-oxopropyl]amino]propanoic acid

A stirred suspension of β-alanine (1.34 g, 15 mmol) in 30 mL of dry acetonitrile under argon was cooled to 0°–5° C. and bis(trimethylsilyl)trifluoroacetamide (8.0 mL, 30 mmol) was added. The reaction mixture was allowed to gradually warm to 6°–7° C. over 1 hour, during which time all of the amino acid went into solution. 2-Trifluoromethyl-3-acetylthio propionyl chloride (3.52 g, 15 mmol) was dissolved in 6 mL of acetonitrile and added dropwise to the mixture at 5° C. over a period of 45 minutes, after which time the reaction mixture was allowed to stir and warm to room temperature. After 1.5 hours, the solvent was evaporated, the yellow residual liquid was partitioned between water (50 mL) and ethyl-acetate (50 mL), and the organic layer was separated. The aqueous phase was further extracted with ethyl acetate (3×40 mL) and the combined ethyl acetate extract was washed with brine, dried over anhydrous magnesium sulfate and evaporated to yield 6.7 g of yellow solid. Flash chromatography on silica gel (100:1 silica gel to compound) using methylene chloride:methanol: acetic acid, 40:1:1 as the eluent gave 1.62 g of material which was homogenous by TLC, as well as 0.65 g of material which was nearly homogenous and 1.16 g of material which was impure but contained mostly the desired product. The 0.65 g and 1.62 g portions of product were triturated with hexanes:ethyl acetate (4:1) to give 2.21 g of the racemic title product as a white crystalline solid, m.p. 114°–116° C., TLC R$_f$=0.44 (20:1:1 methylene chloride:methanol:acetic acid).

Analysis calc'd for C$_9$H$_{12}$F$_3$NO$_4$S: C, 37.63; H, 4.21; N, 4.88; F, 19.84; S, 11.16; Found: C, 37.62; H, 4.12; N, 4.83; F, 19.77; S, 11.38.

EXAMPLE 12

[3-[[2-(Mercaptomethyl)-3,3,3-trifluoro-1-oxopropyl]amino]propanoic acid

A suspension of the title compound of Example 11 (2.08 g, 7.24 mmol) in 4.2 mL of concentrated ammonium hydroxide and 9.3 mL of water was stirred at room temperature under argon for 7–10 minutes, during which period a clear solution was formed. The solution was acidified to a pH of 2 with approximately 200 mL of 5 percent potassium hydrogen sulfate and extracted with ethyl acetate (5×50 mL). The combined ethyl acetate extract was washed with 50 mL of brine, dried over anhydrous magnesium sulfate and evaporated to give 1.74 g of an off-white solid. Flash chromatography on silica gel (120:1 silica gel to compound) using methylene chloride:methanol: acetic acid, 40:1:1 as the eluent gave 1.50 g of compound. Similarly, a 1.2 g impure fraction of the same starting material (nominally 4.2 mmol), on deacylation and flash chromatography, afforded another 0.45 g of the desired product. The two fractions of product were combined to afford 1.95 g of the title racemic compound as a white crystalline solid, m.p. 108°–110° C., TLC R$_f$=0.40 (20:1:1 methylene chloride:methanol:acetic acid).

Analysis calc'd for C$_7$H$_{10}$F$_3$NO$_3$S: C, 34.28; H, 4.11; N, 5.71; F, 23.24; S, 13.07; SH, 13.49; Found: C, 34.36; H, 4.04; N, 5.58; F, 22.94; S, 13.07; SH, 13.64.

EXAMPLE 13

N-[3,3,3-Trifluoro-2-(mercaptomethyl)-1-oxopropyl]-L-aspartic acid a)

N-[2-[(Acetylthio)methyl]-3,3,3-trifluoro-1-oxopropyl]-L-aspartic acid

A stirred suspension of L-aspartic acid (2.66 g., 20 mmol.) in 35 mL of dry acetonitrile under argon was cooled to 0° C. and bis(trimethylsilyl)trifluoroacetamide (10.62 mL, 40 mmol) was added. The reaction mixture was allowed to stir and gradually warmed to room temperature overnight, and then 5 mL of dimethylformamide was added and the mixture was stirred for 2 hours. The resultant clear, light yellow solution was cooled to 5° C. and 2-trifluoromethyl-3-acetylthiopropionyl chloride (4.69 g., 20 mmol), dissolved in 6 mL of acetonitrile, was added dropwise. The reaction mixture was allowed to stir and warm to room temperature overnight, and then the solvent was evaporated. The yellow syrupy residue was partitioned between water (50 mL) and ethyl acetate (50 mL), and the organic layer was separated. The aqueous phase was further extracted with ethyl acetate (3×50 mL) and the combined ethyl acetate extract was washed with brine, dried (MgSO$_4$) and evaporated to yield 12.2 g. of a light yellow residue. Flash chromatography on silica gel (125:1 silica gel to compound) eluting with ethyl acetate:acetic acid, 15:1 gave 5.25 g. of a major fraction which was a light yellow sticky solid and 0.63 g. fraction which was nearly homogeneous by TLC, for a total of 5.88 g. of the title compound as a mixture of diastereomers.

b)

N-[3,3,3-Trifluoro-2-(mercaptomethyl)-1-oxopropyl]L-aspartic acid

A suspension of the product from part (a) (4.68 g., 14.1 mmol.) in 8.25 mL of concentrated ammonium hydroxide and 20.6 mL of water was stirred at room temperature under argon for approximately 10 minutes. The resulting solution was acidified with 400 mL of 5% potassium hydrogen sulfate and extracted with ethyl acetate (4×75 mL). The combined ethyl acetate extract was washed with brine, dried (MgSO$_4$), and evaporated to give 3.41 g. of light yellow solid. Flash chromatography on 350 g. of silica gel eluting with methylene chloride:methanol:acetic acid, 15:1:1 gave 2.4 g. of a slightly yellow solid which was triturated with methylene chloride containing a few drops of ethyl acetate and methanol to give 2.1 g. of the title compound (an approximately 1:1 mixture of diastereomers) as a white crystalline solid, m.p., 180°–183° C., TLC R$_f$=0.31 (10:1:1 methylene chloride: methanol:acetic acid), [α]$_D$=−1.9° (c=1.00, methanol).

Analysis calc'd for $C_8H_{10}F_3NO_5S \cdot 0.25\ H_2O$: C, 32.70; H, 3.60; N, 4.77; F, 19.40; S, 10.91; SH, 11.26; Found: C, 32.64; H, 3.20; N, 4.70; F, 19.23; S, 10.85; SH, 11.15.

EXAMPLE 14

N-[2-[(Acetylthio)methyl]-3,3,3-trifluoro-1-oxopropyl]-L-($\beta$)-naphthylalanine, isomer A A stirred suspension of L-naphthylalanine (1.92 g., 8.92 mL) in 40 mL of acetonitrile under argon was cooled to 0°–5° C. and bis(trimethylsilyl)trifluoroacetamide (4.75 mL, 17.84 mmol) was added. The reaction mixture was allowed to stir and gradually warm to room temperature. After 1.5 hours, an additional 2.3 mL of bis(trimethylsilyl)trifluoroacetamide (8.7 mmol.) was added which resulted in a clear solution in 20 minutes. The reaction mixture was cooled to 5° C. and 2-trifluoromethyl-3-acetylthiopropionyl chloride (2.09 g., 8.92 mmol.) dissolved in 6 mL of acetonitrile was added dropwise and the mixture gradually warmed to room temperature. After an hour, the reaction mixture was evaporated to a yellow solid residue, partitioned between water (50 mL) and ethyl acetate (75 mL) and the organic layer was separated. The aqueous layer was extracted with additional ethyl acetate (3×45 mL) and the combined ethyl acetate extract was washed with brine, dried (MgSO$_4$), and ethyl acetate removed in vacuo to give 6.3 g. of light yellow solid residue. This crude material was flash chromatographed over 700 g. of silica gel eluting with ethyl acetate:hexanes:acetic acid, 100:100:1 which gave 1.58 g. of fast eluting isomer A and 1.56 g. of slow eluting isomer B. A 300 mg. portion of isomer A was crystallized from hexanes: ethyl acetate (2:1) to give 160 mg. of title isomer A compound as a white long needle crystalline solid, m.p. 162°–164° C., TLC R$_f$=0.29 (100:50:1 ethyl acetate: hexane:acetic acid), $[\alpha]_D = -79.2°$ (c=1.00, methanol).

Analysis calc'd for $C_{19}H_{18}F_3NO_4S$: C, 55.20; H, 4.39; N, 3.39; F, 13.79; S, 7.76; Found: C, 55.02; H, 4.15; N, 3.29; F, 13.60; S, 7.54.

EXAMPLE 15

N-[2-[(Acetylthio)methyl]-3,3,3-trifluoro-1-oxopropyl]-L-($\beta$)-naphthylalanine, isomer B The isomer B product from Example 14 was flash chromatographed again using ethyl acetate: acetic acid (200:1.5) and ethyl acetate:hexanes: acetic acid (100:50:1) as the eluent to remove isomer A impurity and give 1.4 g. of title isomer B compound as a white solid, m.p. 166°–169° C., TLC R$_f$=0.15 (100:50:1 ethyl acetate:hexane: acetic acid ) $[\alpha]_D= +116.3°$ (c=1.00, methanol).

Analysis calc'd for $C_{19}H_{18}F_3NO_4S$: C, 55.20; H, 4.39; N, 3.39; F, 13.79; S, 7.76; Found: C, 54.96; H, 4.39; N, 3.35; F, 13.75; S, 7.83.

EXAMPLE 16

(S)-$\alpha$-[[3,3,3-Trifluoro-2-(mercaptomethyl)-1-oxopropyl]amino]-2-naphthalenepropanoic acid, isomer A A suspension of the product of Example 14, 2.01 g., 4.86 mmol) in 3.2 mL of concentrated ammonium hydroxide and 8.0 mL of water was stirred at room temperature under argon for 8 minutes. The clear solution was acidified with 5% potassium hydrogen sulfate solution to pH of about 2 and extracted with ethyl acetate (4×50 mL). The combined ethyl acetate extract was washed with brine, dried (MgSO$_4$), and evaporated to give 1.72 g. of light yellow waxy solid. Flash chromatographic purification of this crude product over silica gel (150:1 silica gel to compound) eluting with ethyl acetate:hexanes:acetic acid (100:50:1) gave 1.42 g. of white crystalline product which on treatment with toluene and drying under vacuum afforded 1.24 g. of the title isomer A compound as a white solid, m.p. 165°–167° C., TLC R$_f$=0.26 (100:50:1 ethyl acetate: hexane:acetic acid), $[\alpha]_D= +31.9°$ (c=1.00, methanol).

Analysis calc'd for $C_{17}H_{16}F_3NO_3S$: C, 54.98; H, 4.34; N, 3.77; F, 15.35; S, 8.63; SH, 8.90; Found: C, 55.17; H, 4.29; N, 3.63; F, 15.42; S, 8.68; SH, 9.18.

EXAMPLE 17

(S)-$\alpha$-[[3,3,3-Trifluoro-2-(mercaptomethyl)-1-oxopropyl]amino]-2-naphthalenepropanoic acid, isomer B A solution of the product of Example 15 (1.4 g.) in 10 mL of methanol was treated with a solution of hydroxylamine hydrochloride (0.552 g., 7.94 mmol) in 7.9 mL of 1N sodium hydroxide and stirred at room temperature under argon. The reaction was complete in 35 minutes as judged by TLC. The reaction mixture was evaporated, the resulting white solid was taken up in 25 mL of water and extracted with ethyl acetate (4×35 mL). The combined organic extract was washed with 50 mL of brine, dried (MgSO$_4$) and evaporated to give 1.4 g. of white solid. Flash chromatography of this crude product on silica gel (180:1 silica gel to compound) eluting with ethyl acetate:hexanes:acetic acid, 100:50:1) gave 1.24 g. of the title isomer B compound as a white crystalline solid, m.p. 172°–179° C. TLC R$_f$=0.19 (100:50:1 ethyl acetate:hexane:acetic acid), $[\alpha]_{DD}= +71.3°$ (c=1.00, methanol)

Analysis calc'd for $C_{17}H_{16}F_3NO_3S$: C, 54.98; H, 4.34; N, 3.77; F, 15.35; S, 8.63; SH, 8.90; Found: C, 55.02; H, 4.30; N, 3.55; F, 15.18; S, 8.64; SH, 9.09.

EXAMPLE 18

N-[2-[(Acetylthio)methyl]-3,3,3-trifluoro-1-oxopropyl]-L-leucine, isomer A

A stirred suspension of L-leucine (2.62 g., 20 mmol) in 35 mL of dry acetonitrile under argon was cooled to 0°–5° C. and bis(trimethylsilyl)trifluoroacetamide (10.62 mL, 40 mmol) was added. The reaction mixture was allowed to stir while slowly warming to room temperature. After 2 hours, another 3.5 mL (13 mmol) of bis(trimethylsilyl)trifluoroacetamide was added which resulted in a clear lemon color solution on additional stirring for one hour at room temperature. The reaction mixture was cooled to 0°–5° C. and 2-trifluoromethyl-3-acetylthiopropionyl chloride (4.69 g., 20 mmol.) dissolved in 8 mL of acetonitrile was added dropwise over 45 minutes. After stirring for 1.5 hours at 0°–5° C. to room temperature, TLC shows completion of the reaction. The reaction mixture was evaporated under reduced pressure to give a yellow oily residue which was partitioned between ethyl acetate (75 mL) and water (50 mL). The aqueous phase was further extracted with ethyl acetate (4×50 mL), the combined extracts were washed with 75 mL of brine, dried (MgSO$_4$), and evaporated to give 10.3 g. of a yellow semi-solid residue. A 0.68 g. portion of this crude material was flash chromatographed on 75 g. of silica gel eluting with ethyl acetate: hexanes:acetic acid, 100:100:1 to yield 0.15 g. of the faster eluting diastereomer (isomer A) and 0.12 g. of slower eluting diastereomer (isomer B). The remaining 9.6 g. of crude material was flash chromatographed similarly (silica gel, 1300 g.) which gave 2.5 g. of isomer A, 2.7 g. of a mixture of both the diastereomers, and 1.5 g. of isomer B. The mixed fractions were rechromatographed using the same conditions to give 0.5 g. of isomer A and 1.25 g. of isomer B. Both the 2.5 g. and 0.5 g. portions of isomer A were combined, triturated with hexanes containing a few drops of ethyl acetate, filtered, and dried to yield 2.57 g. of the title isomer A product as a white crystalline solid, m.p. 150°–152° C., TLC $R_f$=0.40 (100:50:1 ethyl acetate:hexane:acetic acid), $[\alpha]_D$= −146.9° (c=1.00, methanol).

Analysis calc'd for $C_{12}H_{18}F_3NO_4S$: C, 43.76; H, 5.51; N, 4.25; F, 17.31; S, 9.73; Found: C, 43.79; H, 5.50; N, 3.96; F, 17.10; S, 9.81.

EXAMPLE 19

N-[2-[(Acetylthio)methyl]-3,3,3-trifluoro-1-oxopropyl]-L-leucine, isomer B

A portion of isomer B from Example 18 (2.61 g.) was triturated twice with hexanes containing a few drops of ethyl acetate and once with hexanes:ether (3:1) which afforded on filtering and drying 1.6 g. of the title isomer B product as a white crystalline solid; m.p. 110°–113° C., TLC $R_f$=0.27 (100:50:1 ethyl acetate:hexanes:acetic acid) $[\alpha]_D$= +109.6° (c=1.00, methanol).

Analysis calc'd for $C_{12}H_{18}F_3NO_4S$: C, 43.76; H, 5.51; N, 4.25; F, 17.31; S, 9.73; Found: C, 43.80; H, 5.56; N, 3.92; F, 17.03; S, 9.42.

EXAMPLE 20

N-[3,3,3-Trifluoro-2-(mercaptomethyl)-1-oxopropyl]-L-leucine, isomer A

A suspension of the product of Example 18 (2.3 g., 6.98 mmol.) in 4.45 mL of concentrated ammonium hydroxide and 10 mL of water was stirred at room temperature under argon for 8 minutes. The resulting clear solution was acidified with 5% potassium hydrogen sulfate solution to pH 2 and extracted with 100 mL of ethyl acetate followed by 3×75 mL of additional extractions. The combined ethyl acetate extract was washed with 100 mL of brine, dried (MgSO₄) and evaporated to give 1.94 g. of an off-white solid. Flash chromatography on 200 g. of silica gel eluting with ethyl acetate: hexanes:acetic acid, 100:100:1 afforded 1.72 g. of the title isomer A product as a white crystalline solid, m.p. 143°–145° C., TLC $R_f$=0.38 (100:50:1 ethyl acetate:hexane:acetic acid), $[\alpha]_D$= −62.2° (c=1.00, methanol).

Analysis calc'd for $C_{10}H_{16}F_3NO_3S$: C, 41.80; H, 5.61; N, 4.88; F, 19.84; S, 11.16; SH, 11.51; Found: C, 41.89; H, 5.62; N, 5.12; F, 19.51; S, 11.05; SH, 11.78.

EXAMPLE 21

N-[3,3,3-Trifluoro-2-(mercaptomethyl)-1-oxopropyl]-L-leucine, isomer B

A suspension of the product of Example 19, (1.3 g., 3.95 mmol.) in 2.52 mL of concentrated ammonium hydroxide and 5.6 mL of water was stirred at room temperature under argon for 8 minutes. The clear solution was acidified with 5% potassium hydrogen sulfate solution (120 mL) to pH 2 and extracted with 75 mL of ethyl acetate followed by additional 3×40 mL portions of ethyl acetate. The combined ethyl acetate extract was washed with 50 mL of brine, dried (MgSO₄), and evaporated to give 1.04 g. of light yellow solid. This material was combined with 35 mg. prepared in a similar way. This combined crude material was purified by flash chomatography on 200 g. of silica gel eluting with ethyl acetate:hexanes:acetic acid, 100:100:1 which afforded 0.93 g. of the title isomer B product as a white crystalline solid, m.p. 132°–134° C., TLC $R_f$=0.33 (100:50:1 ethyl acetate:hexane:acetic acid) , $[\alpha]_D$= +4.8° (c=1.00, methanol).

Analysis calc'd for $C_{10}H_{16}F_3NO_3S$: C, 41.80; H, 5.61; N, 4.88; F, 19.84; S, 11.16; SH, 11.51; Found: C, 41.83; H, 5.66; N, 5.04; F, 19.67; S, 11.13; SH, 11.79.

EXAMPLE 22

2-(Acetylthiomethyl)-3,3,3-trifluoro-N-[2-(4-hydroxyphenyl)ethyl]propanamide

To a stirred solution of 4-(2-aminoethyl)phenol (4.60 g, 36.2 mmol) in 250 mL of dry methylene chloride maintained at −10° C. was added a solution of 2-trifluoromethyl-3-acetylthio propionyl chloride (4.24 g, 18.1 mmol) in 50 mL of dry methylene chloride and then the reaction was stirred at −10° C. for 3 hours. The reaction mixture was washed three times with 1N hydrochloric acid, and the organic layer was dried over anhydrous magnesium sulfate, filtered and concentrated in vacuo to yield 3.5 g of a yellow oil. The crude material was flash chromatographed on 400 mL of LPS-1 silica gel using 2:1 hexane:ethyl acetate as the eluent; isolation of product afforded 1.6 g of the title compound as a clear oil. TLC $R_f$=0.12 (4:1 EtOAc:CH₂Cl₂).

Analysis calc'd for $C_{14}H_{16}F_3NO_3S \cdot 1.1 H_2O$: C, 49.61; H, 4.88; N, 4.13; F, 16.82; S, 9.46; Found: C, 49.38; H, 4.77; N, 4.34; F, 16.58; S, 9.51.

EXAMPLE 23

2-(Mercaptomethyl)-3,3,3-trifluoro-N-[2-(4-hydroxyphenyl)ethyl]propanamide

A solution of the title compound of Example 22 (1.6 g.) in 20 mL of methanol was treated with a solution of 1N ammonium hydroxide (9 mL, 9.0 mmol) and then stirred at room temperature for 3 hours. The reaction mixture was partitioned between ether and 1N hydrochloric acid, and the layers separated. The organic layer was washed with 1N hydrochloric acid and brine, dried over anhydrous magnesium sulfate, filtered and concentrated in vacuo to yield 1.40 g of a glassy yellow solid. The crude material was flash chromatographed on 300 mL of LPS-1 silica gel using 97:3 methylene chloride: methanol as the eluent, to afford 0.74 g of the title compound as a white solid, m.p. 98°–100° C.

Analysis calc'd for C, 48.84; H, 4.85; N, 4.75; F, 19.32; S, 10.87; SH, 11.23; Found: C, 48.97; H, 4.63; N, 4.62; F, 18.96; S, 10.76; SH, 10.93.

EXAMPLE 24

2-(Acetylthiomethyl)-3,3,3-trifluoro-N-[2-(4-pyridinyl)ethyl]propanamide

To a stirred solution of 4-(2-aminoethyl)pyridine (4.60 g, 37.7 mmol) in 250 mL of dry methylene chloride maintained at −10° C. was added a solution of 2-trifluoromethyl-3-acetylthiopropionyl chloride (4.38 g, 18.7 mmol) in 50 mL of dry methylene chloride and then the reaction was stirred at −10° C. for 3 hours. The reaction mixture was washed four times with 5% sodium hydrogen carbonate, and the organic layer was dried over anhydrous magnesium sulfate, filtered and concentrated in vacuo to yield 5.62 g of a yellow solid. The crude material was flash chromatographed on 700 mL of LPS-1 silica gel using 4:1 ethyl acetate:methylene chloride as the eluent; isolation of product afforded 4.42 g of the title compound as a light yellow solid, m.p. 87°–89° C.

Analysis calc'd for $C_{13}H_{15}F_3N_2O_2S$: C, 48.74; H, 4.72; F, 17.79; N, 8.75; S, 10.01; Found: C, 48.67; H, 4.64; F, 17.60; N, 8.73; S, 10.04.

EXAMPLE 25

2-(Mercaptomethyl)-3,3,3-trifluoro-N-[2-(4-pyridinyl)ethyl]propanamide, hydrochloride A solution of the product of Example 24 (2.0 g., 6.2 mmol.) in 30 mL of 1:1 methanol/water was chilled to 0° C. and treated with 5 mL of $NH_4OH$ (14.8M, 5 mL, 74 mmol) and stirred until the solution became clear, approximately 10 minutes. The reaction was concentrated in vacuo and the residue was taken up in a minimal volume of water (methanol was added to improve solubility) and lyophilized overnight to yield 1.9 g. of a yellow solid. The crude product was flash chromatographed on 350 mL of silica gel eluting with methylene chloride:methanol, 97:3 to afford 1.43 g. of white solid 2-(mercaptomethyl)-3,3,3-trifluoro-N-[2-[4-pyridinyl]ethyl]propanamide as a white solid; m.p. 114°–115° C., TLC $R_f=0.21$ (95:5 methylene chloride/methanol).

Analysis calc'd for $C_{11}H_{13}F_3N_2OS$: C, 47.47; H, 4.71; F, 20.48; N, 10.07; S, 11.52; SH, 11.88 Found: C, 47.62; H, 4.69; F, 20.16; N, 9.88; S, 11.75; SH, 12.06.

A solution of the above product (1.26 g., 4.53 mmol.) in 15 mL of acetonitrile was treated with excess ethereal HCl and stirred for 5 minutes, the volatiles were removed in vacuo to yield a clear oil. Trituration of the oil with hexanes yielded 0.978 g. of the titled compound as a white solid, m.p. 155°–156° C., TLC $R_f=0.17$ (95:5 methylene chloride/methanol).

Analysis calc'd for $C_{11}H_{14}ClF_3N_2OS \cdot 0.07\ H_2O$: C, 41.81; H, 4.51; N, 8.87; F, 18.04; S, 10.15; SH, 10.46; Cl, 11.22. Found: C, 42.02; H, 4.41; N, 8.77; F, 17.64; S, 10.12; SH, 10.64; Cl, 10.94.

EXAMPLE 26

2-[(Acetylthio)methyl]-3,3,3-trifluoro-N-[2-(1 H-tetrazol-5-yl)ethyl]propanamide

A. (N)-t-Butoxycarbonyl-3-aminopropionitrile

3-Aminopropionitrile formate (1.28 g, 10 mmol) was dissolved in 40 mL of absolute ethanol by the addition of diisopropylethylamine (3.48 mL, 20 mmol) at 0° C. After stirring for 10 minutes, di-tert-butyldicarbonate (2.18 g, 10 mmol) was added and the reaction mixture was stirred at room temperature for 48 hours, concentrated in vacuo and the residue was dissolved in ethyl acetate (200 mL). The ethyl acetate solution was washed with water, saturated sodium bicarbonate, dried over sodium sulfate and concentrated in vacuo to yield the title A compound as a solid (1.68 g), m.p. 44°–45° C.

B. 5-((N)-t-butoxycarbonyl-2-aminoethyl)tetrazole

Tri-n-butyltin azide (4.98 g., 15 mmol.) and the title A compound (1.68 g., 9.8 mmol.) were heated at 115° C. in 100 mL of xylene for 48 hours. The reaction mixture was concentrated in vacuo and the residue was dissolved in 2:8 (20:6:11, pyridine:acetic acid:water):ethyl acetate (100 mL). Silica gel (25 g) was added and the mixture was stirred at room temperature overnight. The reaction mixture was filtered and the silica pad washed thoroughly with the above 2:8 (20:6:11, pyridine: acetic acid:water):ethyl acetate solvent system. The filtrate was concentrated in vacuo and the residue was concentrated from toluene (2 x). The product solidified upon addition of isopropyl ether. The product was filtered to yield 1.88 g of the title B compound, (m.p. 121°–126° C.).

C. 5-(2-Aminoethyl)tetrazole hydrochloride

The title B compound (1.88 g, 8.8 mmol) was dissolved in 20 mL of ethyl acetate saturated with HCl. The reaction mixture was stirred for 3 hours and the resulting precipitate was filtered to yield the title C compound (1.04 g) as a solid, m.p. 120°–129° C. (dec.).

D. 2-[(Acetylthio)methyl]-3,3,3-trifluoro-N-[2-(1 H-tetrazol-5-yl)ethyl]propanamide The title C compound (0.92 g, 6.15 mmol) was suspended in 15 mL of dry acetonitrile under argon. Bis(-trimethylsilyl)trifluoroacetamide (5.2 mL, 19.6 mmol) was added and stirred until a clear solution was obtained (2 hours). The reaction mixture was cooled to 5° C., 2-trifluoromethyl-3-acetylthio propionyl chloride (1.44 g, 6.14 mmol) was added dropwise, and the mixture was stirred for 2 hours at 5° to 10° C. The reaction mixture was concentrated in vacuo, dissolved in ethyl acetate (200 mL) and the ethyl acetate solution was washed with water (3 x), pH buffer 4.02, brine (2 x), dried over sodium sulfate and concentrated in vacuo. Addition of isopropyl ether caused solidification. The solid was filtered and dried (1.38 g), m.p. 157°–160° C.

Analysis calc'd for $C_9H_{12}F_3N_5O_2S$: C, 34.72; H, 3.89; N, 22.50; F, 18.31; S, 10.30; Found: C, 34.41; H, 3.80; N, 21.39; F, 18.64; S, 10.34.

EXAMPLE 27

3,3,3-Trifluoro-2-(mercaptomethyl)-N-[2-(1 H-tetrazol-5-yl)ethyl]propanamide The title compound of Example 26 (1.0 g., 3.2 mmol.) was dissolved at 0° C. under argon in 2.5 mL of a 1:1 concentrated $NH_4OH:H_2O$ solution. The reaction mixture was stirred at 0° C. for 5 minutes and then acidified with 5N HCl to pH 6 at 0° C. The product was extracted with ethyl acetate containing 5 percent methanol (3 x) (200 mL portions). The organic layer was washed with brine, dried over sodium sulfate and concentrated in vacuo. The residue was chromatographed through 50 g of Merck silica gel using a (3:3:94) methanol:acetic acid:methylene chloride solvent system. The appropriate fractions were combined and concentrated to yield 0.56 g of the title product, m.p. 182°–184° C.

Analysis calc'd for $C_7H_{10}N_5OSF_3 \cdot 0.13\ H_2O$: C, 30.95; H, 3.81; N, 25.78; F, 20.98; S, 11.80; SH, 12.17; Found: C, 31.15; H, 3.66; N, 25.53; F, 20.58; S, 11.83; SH, 12.21.

EXAMPLE 28

3,3,3-Trifluoro-N-(3-hydroxyphenyl)-2-(mercaptomethyl)propanamide a) 3,3,3-Trifluoro-2-[(acetylthio)methyl]-N-(3-hydroxyphenyl)propanamide

To a solution of 3-aminophenol (4.02 g., 36.8 mmol.) in 250 mL of methylene chloride was added 2-trifluoromethyl-3-acetylthiopropionyl chloride (4.29 g., 18.3 mmol.) and then stirred at −10° C. for 5.5 hours. The reaction mixture was washed with 1 N HCl (3 x)

and then brine, dried (MgSO$_4$), filtered, and concentrated in vacuo to yield 4.58 g. of the title A compound as an off white solid, m.p. 148°–149° C., TLC R$_f$=0.73 (4:1, ethyl acetate:methylene chloride).

b)
3,3,3-Trifluoro-N-(3-hydroxyphenyl)-2-(mercaptomethyl)propanamide

NH$_4$OH (14.8M solution, 2.6 mL, 38.8 mmol.) was added to a solution of the title A compound (1.05 g., 3.42 mmol) in 16 mL of 1:1 water/methanol at 0° C. and stirred for 10 minutes. The reaction was quenched at 0° with 10% potassium bisulfate, and extracted with ethyl acetate (4 x). The organic extracts were combined, dried (MgSO$_4$), filtered, and concentrated in vacuo to yield 1.17 g. of a yellow solid. This crude material was flash chromatographed on 250 mL of EM-60 silica gel eluting with 98:2 methylene chloride/methanol to yield 0.68 g. of the title compound as an off-white solid, m.p. 147°–151° C., TLC R$_f$=0.36 (95:5, methylene chloride/methanol).

Analysis calc'd for C$_{10}$H$_{10}$F$_3$NO$_2$S·0.07 H$_2$O: C, 45.30; H, 3.85; N, 5.21; F, 21.20; S, 11.93; SH, 11.90 Found: C, 45.26; H, 3.81; N, 5.09; F, 20.82; S, 11.72; SH, 12.31.

EXAMPLE 19

N-[2-[(Acetylthio)methyl]-3,3,3-trifluoro-1-oxopropyl]-L-norleucine, isomer A

Bis(trimethylsilyl)trifluoroacetamide (16 mL., 60 mmol.) was added to a suspension of L-norleucine (2.62 g., 20 mmol.) in 40 mL of acetonitrile at 0° C. The suspension was allowed to warm to room temperature and was stirred for 2.5 hours, at which point, almost all of the solid dissolved. The reaction mixture was re-cooled to 0° C. and 2-trifluoromethyl-3-acetylthiopropionyl chloride (4.7 g., 20 mmol.) was added dropwise over 20 minutes as a solution in 10 mL of acetonitrile. After stirring at room temperature for 18 hours, the reaction was poured into 200 mL of water and the resulting mixture was extracted with ethyl acetate (500 mL). Brine was added to break up an emulsion which formed during this extraction. The aqueous layer was extracted once more with ethyl acetate (100 mL) and the combined organic layers were washed with brine, dried (MgSO$_4$), and concentrated to afford an oily residue which was pre-absorbed on Celite. The crude product and Celite mixture was loaded onto an 8×30 cm silica gel column which was eluted as follows: 5 L hexane:ethyl acetate:acetic acid (750:250:25), 2 L hexane:ethyl acetate:acetic acid (700:300:25), 2 L hexane:ethyl acetate:acetic acid (500:500:25). The pure less polar fractions were concentrated and co-evaporated from heptane to afford a white solid which was recrystallized twice from ethyl acetate/hexane. Drying under high vacuum at room temperature for 18 hours afforded 1.95 g. of the title isomer A compound as a white powder, m.p. 176°–178° C., TLC R$_f$=0.30 (ethyl acetate:hexane:acetic acid, 30:70:1). [α]$_D$=−133.3° (c=0.6 methanol).

Analysis calc'd. for C$_{12}$H$_{18}$F$_3$NO$_4$S: C, 43.76; H, 5.51; N, 4.25; F, 17.31; S, 9.73 Found: C, 43.76; H, 5.45; N, 4.35; F, 17.57; S, 9.67.

EXAMPLE 30

N-[2-[(Acetylthio)methyl]-3,3,3-trifluoro-1-oxopropyl]-L-norleucine, isomer B

In the procedure of Example 29, the pure more polar fractions were concentrated to afford a white solid which was recrystallized twice from ethyl acetate/hexane. Drying under high vacuum afforded 1.953 g. of the title isomer B compound, m.p. 123°–125° C., TLC R$_f$=0.19 (ethyl acetate: hexane:acetic acid, 30:70:1). [α]$_D$= +123° (c=0.63, methanol).

Analysis calc'd. for C$_{12}$H$_{18}$F$_3$NO$_4$S: C, 43.76; H, 5.51; N, 4.25; F, 17.31; S, 9.73 Found: C, 43.97; H, 5.45; N, 4.29; F, 17.13; S, 9.89.

EXAMPLE 31

N-[3,3,3-Trifluoro-2-(mercaptomethyl)-1-oxopropyl]-L-norleucine, isomer A

Concentrated ammonium hydroxide (3 mL) was added to a suspension of the product of Example 29 (1.95 g.) in 12 mL of deoxygenated water. The reaction mixture, which became homogeneous in less than one minute, was stirred for 15 minutes. At this time, the pH was adjusted to about 1.5 with potassium bisulfate and the resulting aqueous mixture was extracted with ethyl acetate (2×150 mL). The combined organic layers were washed with brine, dried (MgSO$_4$), and concentrated to afford an oily residue. This residue was flash chromatographed on a 5×12 cm silica gel column using hexane:ethyl acetate: acetic acid, 65:35:1. The pure fractions were concentrated and the residue was co-evaporated from heptane several times to afford a white solid. Trituration with hexane and drying 18 hours under high vacuum afforded 1.175 g. of the title isomer A compound as a white solid, m.p. 96°–98° C., TLC R$_f$=0.38 (ethyl acetate: hexane:acetic acid, 40:60:2). [α]$_D$= −43.2 (c=0.60, methanol).

Analysis calc'd. for C$_{10}$H$_{16}$F$_3$NO$_3$S: C, 41.37; H, 5.67; N, 4.83; F, 19.84; S, 11.16; SH, 11.51 Found: C, 41.68; H, 5.42; N, 4.52; F, 19.53; S, 10.89; SH, 11.78.

EXAMPLE 32

N-[3,3,3-Trifluoro-2-(mercaptomethyl)-1-oxopropyl]-L-norleucine, isomer B

Concentrated ammonium hydroxide (3 mL) was added to a suspension of the product of Example 30 (1.95 g.) in 12 mL of deoxygenated water at room temperature. The reaction mixture became homogeneous within one minute. After stirring for a total of 15 minutes, the reaction mixture was acidified to pH 1.5 with concentrated potassium bisulfate solution. This acidic mixture was extracted with ethyl acetate (2×150 mL). The combined organic layers were washed with brine (100 mL), dried (MgSO$_4$), and concentrated to afford a light yellow residue. This residue was chromatographed on a 5×12 cm silica gel column using ethyl acetate:hexane: acetic acid, 40:60:1 for elution. The pure fractions were concentrated and co-evaporated from heptane to afford a colorless solid which was triturated with hexane. Filtration and drying afforded 1.16 g. of a white solid. This material was recrystallized twice from ethyl acetate/hexane to afford 632 mg. of the title isomer B compound as colorless needles, m.p. 131°–133° C., TLC R$_f$=0.26 (ethyl acetate: hexane:acetic acid, 40:60:2). [α]$_D$= +21.3° (c=0.71, methanol).

Analysis calc'd. for $C_{10}H_{16}F_3NO_3S \cdot 0.1 H_2O$: C, 41.53; H, 5.65; N, 4.84; F, 19.71; S, 11.09; SH, 11.44 Found: C, 41.55; H, 5.61; N, 4.85; F, 19.14; S, 10.99; SH, 13.66.

EXAMPLE 33

(S)-N-[3,3,3-Trifluoro-2-(mercaptomethyl)-1-oxo-propyl]-L-isoleucine a)

N-[2-[(Acetylthio)methyl]-3,3,3-trifluoro-1-oxopropyl]-L-isoleucine

Bis(trimethylsilyl)trifluoroacetamide (16 mL, 60 mmol.) was added to a suspension of L-isoleucine (2.62 g., 20 mmol.) in 40 mL of acetonitrile at 0° C. The suspension was allowed to warm to room temperature and stirred for 2 hours. At this time approximately one third of the solid had dissolved. An additional amount of bis(trimethylsilyl)trifluoroacetamide (4 mL, 15 mmol.) was added and the mixture was stirred for 45 minutes. The mixture was cooled to 0° C. and 2-trifluoromethyl-3-acetylthiopropionyl chloride (4.7 g., 20 mmol.) was added dropwise over 15 minutes as a solution in 10 mL of acetonitrile. After stirring for 18 hours at room temperature, the reaction mixture was a clear light yellow solution. Approximately 150 mL of water was added and the resulting mixture was extracted with ethyl acetate (2×150 mL). The combined organic layers were washed with brine (100 mL), dried (MgSO₄), and concentrated to afford an oily residue which was preadsorbed onto Celite for chromatography. After several chromatographies, triturations and recrystallizations 1.41 g. of (R)-N-[2-[(acetylthio)methyl]-3,3,3-trifluoro-1-oxopropyl]-L-isoleucine; m.p. 81°-85° C., $[\alpha]_D = -105.5°$ (c=0.38, methanol) were isolated and 1.56 g. of (S)-N-[2-[(acetylthio)methyl]-3,3,3-trifluoro-1-oxopropyl]-L-isoleucine, m.p. 111°-112° C., $[\alpha]_D = +122.6°$ (c=0.38, methanol) were isolated.

b)

(S)-N-[3,3,3-Trifluoro-2-(mercaptomethyl)-1-oxo-propyl]-L-isoleucine

Concentrated ammonium hydroxide (3 mL) was added to a suspension of the (S) diastereomer product of part (a) (1.5 g., 4.55 mmol.) in 12 mL of deoxygenated water. Dissolution occurred in a few seconds and the reaction mixture was allowed to stir under argon for 5 minutes. The mixture was then acidified to pH 1.5 with potassium bisulfate solution and extracted with ethyl acetate (2×150 mL). The combined organic layers were washed with brine, dried (MgSO₄), and concentrated. The residue was chromatographed on a 5×15 cm silica gel column eluting with hexane:ethyl acetate:acetic acid, 75:25:1. The pure fractions were concentrated and coevaporated from heptane to afford 1.285 g. of a white solid. This solid was recrystallized three times to afford 0.834 g. of the title (S) diastereomer product, m.p. 130°-131° C., TLC $R_f$=0.43 (ethyl acetate:hexane:acetic acid, 40:60:1) $[\alpha]_D = +35.8°$ (c=0.45, methanol).

Analysis calc'd. for $C_{10}H_{16}F_3NO_3S \cdot 0.10 H_2O$: C, 41.55; H, 5.65; N, 4.85; F, 19.72; S, 11.09; SH, 11.44 Found: C, 41.74; H, 5.62; N, 4.76; F, 19.33; S, 10.95; SH, 13.47.

EXAMPLE 34

(R)-N-[3,3,3-Trifluoro-2-(mercaptomethyl)-1-oxo-propyl]-L-isoleucine

Concentrated ammonium hydroxide (2.6 mL) was added to a suspension of the (R) diastereomer product of Example 33(a) (1.3 g., 3.95 mmol.) in 10 mL of water. Dissolution occurred within one minute and the reaction mixture was allowed to stir under argon for 5 minutes at room temperature. The mixture was then acidified to pH 1.5 with potassium bisulfate solution and extracted with ethyl acetate (2×100 mL). The combined organic layers were washed with brine, dried (MgSO₄), and concentrated. The residue was chromatographed on a 5×25 cm silica gel column eluting with hexane:ethyl acetate:acetic acid, 75:25:1. The pure fractions were concentrated and coevaporated from heptane to afford 1.01 g. of a white solid. This solid required very extensive and thorough trituration with heptane, hexane, and pentane to remove trace amounts of ethyl acetate. After final filtration, this material was dried under high vacuum at 100° C. to afford 0.79 g. of the title (R) diastereomer product as a white solid, m.p. 140°-142° C., TLC $R_f$=0.39 (ethyl acetate:hexane:acetic acid, 40:60:2). $[\alpha]_D = -37.3°$ (c=0.55, methanol)

Analysis calc'd. for $C_{10}H_{16}F_3NO_3S$: C, 41.80; H, 5.61; N, 4.88; F, 19.84; S, 11.16; SH, 11.51 Found: C, 42.18; H, 5.67; N, 5.02; F, 19.36; S, 11.48; SH, 12.29.

EXAMPLE 35

(S,R)-3-[[2-[(Acetylthio)methyl]-3,3,3-trifluoro-1-oxoprgpyl]amino]-5-methylhexanoic acid A solution of 3-[[(2,2-dimethylethyl)oxy]carbonyl]amino-5-methylhexanoic acid, methyl ester [prepared by the Arndt-Eistert scheme, Ondetti et al., J. Med. Chem., Vol. 18, p. 761 (1975)] (5.26 g., 20.3 mmol.) in 100 mL of methanol was treated with a 1N sodium hydroxide solution (40 mL, 40 mmol.) and then stirred at room temperature for 3 hours. The reaction was then concentrated in vacuo and the residue taken up in water. The aqueous solution was washed once with ethyl acetate, and then acidified with 6 N HCl, followed by extraction with ethyl acetate (4 x). The organic extracts were combined, dried (MgSO₄), filtered, and concentrated in vacuo to give 5.68 g. of 3-[[(2,2-dimethylethyl)oxy]carbonyl]amino-5-methylhexanoic acid as a clear oil.

A solution of this acid (0.63 g., 2.57 mmol.) in ethyl acetate (5 mL) was treated with HCl (3.2M solution in ethyl acetate, 25 mL, 80 mmol.) and stirred at room temperature for 3 hours. The reaction was sparged with N₂ and then concentrated in vacuo to yield a white solid, which was triturated with ethyl ether to yield 0.37 g. of 3-amino-5-methylhexanoic acid, hydrochloride, m.p. 125°-126° C.

A solution of this acid, hydrochloride (2.7 g., 14.9 mmol.) in dry acetonitrile maintained at 0° C. was treated with diisopropylamine (2.6 mL, 14.9 mmol.) and bis(trimethylsilyl)trifluoroacetamide (8 mL, 30.1 mmol.) and stirred at 0° C. for 30 minutes. Next a solution of 2-trifluoromethyl-3-acetylthiopropionyl chloride (3.46 g., 14.7 mmol.) in 15 mL of dry acetonitrile was added dropwise over a 15 minute period and then allowed to warm to room temperature overnight. The reaction mixture was concentrated in vacuo and the residue was taken up in ethyl acetate and washed with 1N HCl (3x) followed by brine. The organic layer was dried (MgSO$_4$), filtered, and flash chromatographed on 1800 mL of silica gel eluting with hexane:ethyl acetate:acetic acid, 2:1:0.01 to isolate 2.33 g. of the S,R isomer as the faster moving isomer. The crude material was then triturated several times with hexane:ethyl acetate and finally treated with decolorizing carbon to yield 1.7 g. of the titled (S,R) isomer product, m.p. 102°–103° C., TLC R$_f$=0.34 (hexane:ethyl acetate:acetic acid, 100:100:1). [α]$_D$= −124° (c=0.78, methanol).

Analysis calc'd. for C$_{13}$H$_{20}$F$_3$NO$_4$·0.3 H$_2$O: C, 44.78; H, 5.95; N, 4.02; F, 16.35; S, 9.20 Found: C, 45.02; H, 5.82; N, 3.78; F, 16.62; S, 9.51.

EXAMPLE 36

(S,S)-3-[[2-[(Acetylthio)methyl]-3,3,3-trifluoro-1-oxopropyl]amino]-5-methylhexanoic acid Fractions containing the slower moving isomer from the flash chromatography in Example 35 were pooled and concentrated in vacuo yielding an orange oil which was triturated several times with hexane: ethyl acetate and finally treated with decolorizing carbon to yield 1.2 g. of the title (S,S) isomer product as a white solid, m.p. 124°–125° C., TLC R$_f$=0.28 (hexane:ethyl acetate:acetic acid, 100:100:1). [α]$_D$= +98.4° (c=0.89, methanol).

Analysis calc'd. for C$_{13}$H$_{20}$F$_3$NO$_4$S·0.08 H$_2$O: C, 45.28; H, 5.89; N, 4.06; F, 16.53; S, 9.30 Found: C, 45.35; H, 5.98; N, 3.99; F, 16.35; S, 9.18.

EXAMPLE 37

(S,R)-3-[[3,3,3-Trifluoro-2-(mercaptomethyl)-1-oxopropyl]amino]-5-methylhexanoic acid A suspension of the (S,R) isomer product of Example 35 (1.0 g., 2.9 mmol.) in water maintained at 0° C. under argon was treated with ammonium hydroxide (5M solution, 10 mL, 50 mmol.) and stirred for 5 minutes. The reaction was quenched at 0° C. with 140 mL of 10% potassium bisulfate and then extracted with ethyl acetate (4 x). The organic extracts were combined, dried (MgSO$_4$), filtered, and concentrated in vacuo to yield 1.0 g. of yellow solid. The crude reaction product was flash chromatographed on 200 mL of silica gel eluting with hexane:ethyl acetate (2:1) to isolate 0.61 g. of the title (S,R) isomer product as a white solid, m.p. 155°–156° C., TLC R$_f$=0.19 (hexane:ethyl acetate:acetic acid, 100:100:1). [α]$_D$= −55.5° (c=0.89, methanol).

Analysis calc'd. for C$_{11}$H$_{18}$F$_3$NO$_3$S: C, 43.84; H, 6.02; N, 4.65, F, 18.92; S, 10.64; SH, 10.97 Found: C, 43.81; H, 6.08; N, 4.79; F, 18.52; S, 10.62; SH, 11.37.

EXAMPLE 38

(S,S)-3-[[3,3,3-Trifluoro-2-(mercaptomethyl)-1-oxopropyl]amino]-5-methylhexanoic acid A suspension of the (S,S) isomer product of Example 36 (0.91 g., 2.7 mmol.) in water maintained at 0° C. under argon was treated with ammonium hydroxide (5M solution, 10 mL, 50 mmol.) and stirred for 5 minutes. The reaction was quenched at 0° C. with 140 mL of 10% potassium bisulfate and then extracted with ethyl acetate (4 x). The organic extracts were combined, dried (MgSO$_4$), filtered, and concentrated in vacuo to yield 1.0 g. of a yellow solid. The crude reaction product was triturated with hexane:ethyl acetate to yield 0.78 g. of the title (S,S) isomer as an off white solid; m.p. 155°–156° C., TLC R$_f$=0.18 (ethyl acetate:hexane:acetic acid, 100:100:1). [α]$_D$= +26.1° (c=0.81, methanol).

Analysis calc'd. for C$_{11}$H$_{18}$F$_3$NO$_3$S: C, 43.84; H, 6.02; N, 4.65; F, 18.92; S, 10.64; SH, 10.97 Found: C, 44.26; H, 6.26; N, 4.62; F, 18.34; S, 10.22; SH 10.71.

EXAMPLE 39

(S,R)-3,3,3-Trifluoro-2-(mercaptomethyl)-N-[3-methyl-1-(1 H-tetrazol-5-yl)butyl]propanamide a) N-[(Phenylmethoxy)carbonyl]-L-leucinamide

To a solution of N-[(phenylmethoxy)carbonyl]-L-leucine (3 g., 11.3 mmol.) in 60 mL of methylene chloride at −20° under argon was added N-methylmorpholine (1.24 mL, 11.3 mmol.) followed by isobutylchloroformate (1.47 mL, 11.3 mmol.). The resulting suspension was stirred at −20° C. for 15 minutes at which time a solution of ammonia/methanol (about 5.6M, 20 mL, 113 mmol.) was added. After 30 minutes at −20° C., the reaction was quenched with water and warmed to room temperature. The layers were separated and the aqueous layer was extracted with methylene chloride (2 x). The combined organic extracts were dried (MgSO$_4$) and evaporated to give 2.82 g. of the title A compound.

b) N-[(Phenylmethoxy)carbonyl]-L-leucinenitrile

To a solution of the title A compound (9.25 g., 34.9 mmol) in 100 mL of anhydrous tetrahydrofuran at room temperature under argon was added methoxycarbonylsulfamoyltriethylammonium hydroxide inner salt (11.83 g., 9.65 mmol.) in five equal portions over 2 hours. The reaction mixture was poured onto a flash chromatography column eluting with hexanes:ethyl acetate (60:40) to give 4.6 g. of the title B compound as an oil. TLC R$_f$=0.57 (ethyl acetate: hexane, 1:1). [α]$_D$= −49.7° (c=0.82, methanol).

c) (S)-[3-Methyl-1-(1H-tetrazol-5-yl)butyl]carbamic acid, phenylmethyl ester A solution of the title B compound (2.98 g., 12.10 mmol.) and tributyltin azide (6.1 g., 18.14 mmol.) in 100 mL of xylenes was stirred at 110° C. for 2 hours. The mixture was cooled to room temperature and poured directly onto a flash chromatography column eluting with 1 L of hexanes:ethyl acetate (60:40), 2 L of (60:40) hexanes:ethyl acetate plus 2% acetic acid to give 2.23 g. of the title C compound as a viscous oil.

d) (S)-α-(2-Methylpropyl)-1 H-tetrazole-5-methanamine, hydrochloride

A suspension of the title C compound (2.84 g., 9.81 mmol.) in 100 mL of methanol containing acetyl chloride (1.14 mL, 19.62 mmol.) and 20% palladium on carbon catalyst (0.28 g.) was stirred under an atmosphere of hydrogen (balloon) at room temperature. After 4 hours, an additional amount of 20% palladium on carbon catalyst (0.28 g.) and acetyl chloride (1.14 mL) was added. After 22 hours, the reaction mixture was filtered and evaporated. Trituration with hexanes gave 1.88 g. of the title D compound as a white foam.

e) (S,R)-2-[(Acetylthio)methyl]-3,3,3-trifluoro-N-[3-methyl-1-(1 H-tetrazol-5-yl)butyl]-propanamide To a solution of the title D compound (1.73 g., 9.9 mmol.) in 22 mL of acetonitrile at 0° C. under argon was added bis(trimethylsilyl) trifluoroacetamide (7.67 mL, 31.36 mmol.) and the resulting cloudy solution was stirred at room temperature for 2 hours. The reaction mixture was cooled back to 0° C. at which time 2-trifluoromethyl-3-acetylthiopropionyl chloride (2.1 g., 9.8 mmol.) in acetonitrile (6 mL) was added. After stirring the light-yellow solution for 2 hours at 0° C., the reaction was quenched by pouring into 200 mL of water and then extracted with ethyl acetate (2×250 mL). The combined organic extracts were flash chromatographed (90 mm×10 inch—60:40 hexanes:ethyl acetate +2% acetic acid, 90 mm×7 inch—1:1 hexanes:ethyl acetate +0.5% acetic acid, 90 mm×12 inch—1:1 hexanes:ethyl acetate +0.5% acetic acid, 50 mm×10 inch—1:1 hexanes:ethyl acetate +0.5% acetic acid) to give, after recrystallization from ethyl acetate/hexanes, 1.10 g. of the (S,R) isomer title E compound, m.p. 188°–191° C., TLC $R_f$=0.22 (1:1 hexanes/ethyl acetate +0.5% acetic acid), $[\alpha]_D$=−163.8° (c=0.53, methanol) and 1.15 g. of (S,S)-2-[(acetylthio)methyl]-3,3,3-trifluoro-N-[3-methyl-1-(1 H-tetrazol-5-yl)butyl]propanamide, m.p. 180°–184° C., TLC $R_f$=0.16 (1:1 hexanes/ethyl acetate +0.5% acetic acid), $[\alpha]_D$=+60.6° (c=0.51, methanol).

f)
(S,R)-3,3,3-Trifluoro-2-(mercaptomethyl)-N-[3-methyl-1-(1 H-tetrazol-5-yl)butyl]propanamide To a suspension of the (S,R) isomer compound of title E (0.98 g., 2.8 mmol.) in 5.65 mL of degassed water at room temperature under argon was added a mixture concentrated NH$_4$OH (1.85 mL) and water (1.85 mL). After two minutes, the reaction is quenched with saturated potassium bisulfate (pH 1.5) and extracted with ethyl acetate. The organic extracts were dried and purified by flash chromatography (50 mm×6 inch, 1:1 hexanes:ethyl acetate +0.5% acetic acid) to give 0.72 g. of white solid product. This material was triturated with heptane and dried under high vacuum at 100° C. to give 0.7 g. of the title (S,R) product, m.p. 189°–193° (dec.), TLC $R_f$=0.18 (1:1, ethyl acetate:hexane +0.5% acetic acid). $[\alpha]_D$=−97.7° (c=0.57, methanol).

Analysis calc'd. for C$_{10}$H$_{16}$F$_3$N$_5$OS·0.1 CH$_3$COOC$_2$H$_5$: C, 39.02; H, 5.29; N, 21.88; F, 17.80; S, 10.01; SH, 10.33. Found: C, 39.25; H, 5.35; N, 21.54; F, 17.60; S, 10.17; SH 10.62.

EXAMPLE 40

(S,S)-3,3,3-Trifluoro-2-(mercaptomethyl)-N-[3-methyl-1-(1 H-tetrazol-5-yl)butyl]propanamide To a suspension of (S,S)-2-[(acetylthio)methyl]-3,3,3-trifluoro-N-[3-methyl-1-(1 H-tetrazol-5-yl)butyl]propanamide [prepared in Example 39(e), 1.034 g., 2.95 mmol.] in 6 mL of degassed water at room temperature under argon was added a mixture of concentrated NH$_4$OH (1.95 mL) and water (1.95 mL). After two minutes, the reaction was quenched with saturated potassium bisulfate (pH 1.5) and extracted with ethyl acetate. The organic extracts were dried and purified by flash chromatography (50 mm×6 inch, 1:1 hexanes: ethyl acetate +0.5% acetic acid) to give 0.76 g. of white solid product. This material was combined with 25 mg. from a previous experiment and recrystallized from ethyl acetate/hexanes to give 0.69 g. of the title (S,S) isomer product as a white solid, m.p. 183°–184° C., TLC $R_f$=0.14 (1:1, hexanes:ethyl acetate +0.5% acetic acid). $[\alpha]_D$=−39.8° (c=0.57, methanol).

Analysis calc'd. for C$_{10}$H$_{16}$F$_3$N$_5$OS: C, 38.58; H, 5.18; N, 22.50; F, 18.31; S, 10.30; SH, 10.62 Found: C, 38.70; H, 5.27; N, 22.43; F, 17.67; S, 10.28; SH, 11.52.

EXAMPLE 41

(S,R)-β-[[2-[(Acetylthio)methyl]-3,3,3-trifluoro-1-oxopropyl]amino]benzenebutanoic acid a)
(S)-3-[[[(1,1-Dimethylethyl)oxy]carbonyl]amino]-2-oxo-1-diazo-4-phenylbutane A solution of N-[[(1,1-dimethylethyl)oxy]carbonyl]-L-phenylalanine (20.01 g., 75 mmol) in 150 mL of dry tetrahydrofuran was chilled to −25° C. and treated with N-methylmorpholine (8.3 mL, 75 mmol) and isobutylchloroformate (9.8 mL, 75 mmol) and then stirred at −25° C. for 10 minutes. The reaction mixture was then filtered into a flask containing a solution of diazomethane (prepared from 35.48 g., 240 mmol of N-methyl-N'-nitro-N-nitrosoguanidine) in 300 mL of anhydrous ether at −78° C. and then let warm to −5° C. and stirred overnight. The cold reaction mixture was then filtered and the filtrate was washed with water, saturated sodium bicarbonate, and brine. The organic layer was dried (MgSO$_4$), filtered and concentrated in vacuo to yield a reddish brown oil. The oil was triturated with cold petroleum ether to yield 14.42 g. of a light tan solid. The mother liquors were concentrated and allowed to stand yielding a second crop of 1.96 g. of light yellow crystals for a total yield of 16.38 g. of the title A compound as a tannish solid; m.p. 87°–90° C. $[\alpha]_D$=−32.2° (c=1.15, methanol).

b)
(S)-3-[[[(2,2-Dimethylethyl)oxy]carbonyl]amino]-4-phenylbutanoic acid, methyl ester To a solution of the title A compound (13.35 g., 45.9 mmol) in methanol (300 mL) was added dropwise a solution of silver benzoate (1.57 g., 6.85 mmol) in triethylamine (200 mL) and the mixture was stirred for 3 hours. Next, 5 g. of activated charcoal was added and stirred for 15 minutes at room temperature, then the mixture was filtered and the filtrate was concentrated in vacuo to yield a reddish brown oil. The oil was taken up in ether and washed with water, 10% potassium bisulfate, saturated sodium bicarbonate, and brine. The organic layer was dried (MgSO$_4$), filtered, and concentrated in vacuo to yield 11.71 g. of the title B compound as a beige solid, m.p. 50°–52° C., $[\alpha]_D$=−2.0° (c=1.15, methanol).

Analysis calc'd. for C$_{16}$H$_{23}$NO$_4$: C, 65.50; H, 7.90; N, 4.78 Found: C, 65.48; H, 8.04; N, 4.86.

c)
(S)-3-[[[(2,2-Dimethylethyl)oxy]carbonyl]amino]-4-phenylbutanoic acid

A solution of the title B compound (11.0 g., 37.5 mmol) in methanol (200 mL) was treated with 1N solution of sodium hydroxide (75 mL, 75 mmol) and stirred at room temperature for 3.5 hours. The reaction was concentrated in vacuo and the residue was taken up in water, and washed twice with ethyl acetate. The aqueous layer was then acidified with 6N HCl and extracted with ethyl acetate (4 x). The organic extracts were pooled, dried (MgSO$_4$), filtered, and concentrated in vacuo to yield 9.97 g. of the title C compound as a white solid, m.p. 95°–97° C., $[\alpha]_D$=−13.5° (c=0.77, methanol).

Analysis calc'd. for C$_{15}$H$_{21}$NO$_4$·0.48 H$_2$O: C, 62.56; H, 7.79; N, 4.86 Found: C, 62.65; H, 7.45; N, 4.77.

d) (S)-3-Amino-4-phenylbutanoic acid, hydrochloride

A solution of the title C compound (9.45 g., 33.8 mmol) in ethyl acetate (100 mL) was treated with 310 mL of HCl/ethyl acetate (3.2M, 992 mmol) and then stirred at room temperature for 3 hours. The reaction mixture was sparged with $N_2$ and then filtered. The filtered solids were washed with ether and then dried to yield 5.96 g. of the title D compound as a white solid, m.p. 204°–205°, $[\alpha]_D = +6.7°$ (c=1 43, methanol).

Analysis calc'd. for $C_{10}H_{14}ClNO_2 \cdot 0.1\ H_2O$: C, 55.24; H, 6.58; N, 6.37; Cl, 16.31 Found: C, 55.54; H, 6.45; N, 6.37; Cl, 16.01.

e) (S,R)-β-[[2-[(Acetylthio)methyl]-3,3,3-trifluoro-1-oxopropyl]amino]benzenebutanoic acid A solution of the title D compound (5.0 g., 23.2 mmol) in acetonitrile (200 mL) was chilled to 0° C. and treated with ethyldiisopropylamine (4.05 mL, 23.3 mmol) and bis(trimethylsilyl)trifluoroacetamide (12.3 mL, 46.3 mmol) and then stirred at 0° C. for 30 minutes. Next a solution of 2-trifluoromethyl-3-acetylthiopropionyl chloride (5.45 g., 23.2 mmol) in acetonitrile (20 mL) was added dropwise and the reaction allowed to warm to room temperature overnight. The reaction was concentrated in vacuo and the residue taken up in ethyl acetate, and washed with 1N HCl (2 x), water, and brine. The organic layer was dried (MgSO₄), filtered, and concentrated in vacuo to yield 14.8 g. of a deep yellow oil. The crude product was triturated three times with hexane/ethyl acetate and treated with decolorizing carbon in ethyl acetate to yield 8.96 g. of a light yellow solid. The crude solid was flash chromatographed on 2 L of silica gel using 125:75:1 hexane/ethyl acetate/acetic acid to elute the (S,R) isomer and then switching to 150:75:1 ethyl acetate/hexane/acetic acid to elute the (S,S) isomer. There was obtained 1.2 g. of the (S,R) isomer, 2.1 g. of mixed fractions, and 1.68 g. of the (S,S) isomer. The (S,S) and (S,R) isomers were each triturated with hexane/ethyl acetate to yield 1.04 g. of the (S,R) isomer and 1.65 g. of the (S,S) isomer. The mother liquors from the trituration of the (S,S) isomer and the mixed fractions were combined and flash chromatographed as described above to isolate 0.41 g. of the (S,R) isomer and 0.9 g. of the (S,S) isomer with 1.25 g. of mixed fractions. The mixed fractions and mother liquors from the (S,R) triturations were again flash chromatographed as described above to isolate 1.34 g. of the (S,R) isomer, 0.31 g. of the (S,S) isomer and 0.6 g. of mixed fractions. The various (S,R) fractions were combined to yield 2.22 g. and the various (S,S) fractions were combined to yield 2.47 g. The (S,R) isomer was then triturated with hexane/ethyl acetate, treated with decolorizing carbon in ethyl acetate, and finally recrystallized from ethyl acetate/hexane to yield 1.31 g. of the title (S,R) isomer product as a white solid, m.p. 171°–172° C., TLC $R_f = 0.28$ (hexane:ethyl acetate:acetic acid, 100:100:1). $[\alpha]_D = -111.5°$ (c=0.75 methanol).

Analysis calc'd. for $C_{16}H_{18}F_3NO_4S$: C, 50.92; H, 4.81; N, 3.71; F, 15.10; S, 8.50 Found: C, 50.63; H, 4.74; N, 3.87; F, 14.91; S, 8.16.

EXAMPLE 42
(S,S)-β-[[2-[(Acetylthio)methyl]-3,3,3-trifluoro-1-oxopropyl]amino]benzenebutanoic acid The (S,S) isomer from Example 41 (e) (2.47 g.) was triturated with hexane/ethyl acetate, treated with decolorizing carbon in ethyl acetate, and finally recrystallized from ethyl acetate/hexane to yield 1.39 g. of the title (S,S) isomer product as a white solid, m.p. 160°–162° C., TLC $R_f = 0.17$ (hexane:ethyl acetate: acetic acid, 100:100:1). $[\alpha]_D = +103.2$ (c=0.69, methanol).

Analysis calc'd. for $C_{16}H_{18}NF_3O_4S \cdot 0.25\ H_2O$: C, 50.31; H, 4.88; N, 3.67; F, 14.92; S, 8.39 Found: C, 50.57; H, 4.67; N, 3.90; F, 14.53; S, 8.05.

EXAMPLE 43
(S,R)-β-[[3,3,3-Trifluoro-2-(mercaptomethyl)-1-oxopropyl]amino]benzenebutanoic acid The product of Example 41 (0.81 g., 2.1 mmol) was dissolved in 5M NH₄OH (10 mL, 50 mmol) at 0° C. under argon and stirred for 5 minutes. The reaction was quenched at 0° C. with 150 mL of 10% potassium bisulfate and then extracted with ethyl acetate (4 x). The organic extracts were combined, dried (MgSO₄), filtered, and concentrated in vacuo to yield 0.94 g. of a yellow solid. The crude product was flash chromatographed on 300 mL of silica gel eluting with 1:1 hexane:ethyl acetate +0.5% acetic acid to give 0.46 g. of a white solid which was a mixture of the desired (S,R) product and corresponding (S,S) material. The mixture was then separated by a reverse phase preparative HPLC on a YMC-ODS S-10 column using 50% (90% methanol, 10% water with 0.1% trifluoroacetic acid) and 50% (90% water, 10% methanol with 0.1% trifluoroacetic acid) at a flow rate of 63 mL/min. to isolate 0.36 g. of the title (S,R) isomer as a tan solid, m.p. 208°–210° C., TLC $R_f = 0.19$ (hexane: ethyl acetate:acetic acid, 100:100:1). $[\alpha]_D = -38.9°$ (c=0.70, methanol).

Analysis calc'd. for $C_{14}H_{16}F_3NO_3S \cdot 0.25\ H_2O$: C, 49.47; H, 4.90; N, 4.12; F, 16.77; S, 9.43; SH, 9.73 Found: C, 49.21; H, 4.48; N, 4.04; F, 16.40; S, 9.52, SH, 9.49.

EXAMPLE 44
(S,S)-β-[[3,3,3-Trifluoro-2-(mercaptomethyl)-1-oxopropyl]amino]benzenebutanoic acid The (S,S) isomer product of Example 42 (1.26 g., 3.3 mmol) was dissolved in 5M NH₄OH (20 mL, 100 mmol) and stirred at 0° C. for 5 minutes, and then quenched with 10% potassium bisulfate. The reaction was then extracted with ethyl acetate (4 x) and the organic extracts were combined, dried (MgSO₄), filtered, and concentrated in vacuo to yield 1.16 g. of a yellow residue. The crude product was flash chromatographed on 200 mL of silica gel using 100:100:1 hexane:ethyl acetate: acetic acid as the eluant to isolate 800 mg. of a white solid. This product was then triturated with hexane/ethyl acetate to yield 720 mg. of the title (S,S) isomer product as a white solid, m.p. 177°–178° C., TLC $R_f = 0.10$ (hexane:ethyl acetate:acetic acid, 100:100:1). $[\alpha]_D = +41.6°$ (c=0.55, methanol).

Analysis calc'd. for $C_{14}H_{16}F_3NO_3S \cdot 0.06\ H_2O$: C, 49.98; H, 4.83; N, 4.16; F, 16.94; S, 9.53; SH 9.83 Found: C, 50.11; H, 4.85; N, 4.03; F, 16.56; S, 9.47; SH, 9.74.

EXAMPLE 45

(S)-3-Hydroxy-N-[3,3,3-Trifluoro-2-(mercaptomethyl)-1-oxopropyl]-L-tyrosine a)
(S)-3-Hydroxy-N-[2-[(acetylthio)methyl]-3,3,3-trifluoro-1-oxopropyl]-L-tyrosine Bis(trimethylsilyl)trifluoroacetamide (16 mL, 60 mmol.) was added to a suspension of 3-hydroxy-L-tyrosine (2.37 g., 12 mmol.) in 25 mL of acetonitrile at 0° C. The suspension was stirred for 6 hours at room temperature at which point it was recooled to 0° C. 2-Trifluoromethyl-3-acetylthiopropionyl chloride (2.81 g., 12 mmol.) was added as a solution in 5 mL of acetonitrile and the reaction mixture was stirred at room temperature for 20 hours. After pouring the reaction mixture into about 150 mL of 1N HCl, the biphasic mixture was stirred at room temperature for 30 minutes. At this point, the mixture was extracted with ethyl acetate (2×200 mL) and the combined organic layer was washed with water (200 mL) then brine (100 mL), dried (MgSO4) and then concentrated to an oily residue. After several chromatographies, 1.71 g. of (R)-3-hydroxy-N-[2-[(acetylthio)methyl]-3,3,3-trifluoro-1-oxopropyl]-L-tyrosine, [α]$_D$=−6.5° (c=0.15, methanol), were isolated as a white foam and 1.63 g. of (S)-3-hydroxy-N-[2-[(acetylthio)methyl]-3,3,3-trifluoro-1-oxopropyl]-L-tyrosine, m.p. 175°–184° C., [α]$_D$=+106.3° (c=0.49, methanol), were isolated as an off-white amorphous soild.

b)
(S)-3-Hydroxy-N-[3,3,3-trifluoro-2-(mercaptomethyl)-1-oxopropyl]-L-tyrosine Concentrated ammonium hydroxide (2.5 mL) was added to a suspension of the (S) isomer product of title A (1.4 g., 3.54 mmol.) in deoxygenated water (2.5 mL) at room temperature. After stirring the turbid reaction mixture for one minute, saturated potassium bisulfate solution was added until a pH of about 1.5 was attained. The acidic mixture was extracted with ethyl acetate (2×125 mL) and combined organic layers were washed with brine, dried (MgSO4), and concentrated. The residue was chromatographed on a 5×12 cm silica gel column using ethyl acetate: hexane:acetic acid, 55:45:2 as the mobile phase. The purest fractions were concentrated to afford 997 mg. of a white foam which was rechromatographed on a 5×12 cm silica gel column using ethyl acetate: hexane:acetic acid, 40:60:2 as the mobile phase. The purest fractions were concentrated to a foamy residue which was exhaustively coevaporated from toluene, heptane, methylene chloride, and hexane. The material was triturated thoroughly with heptane and pentane and dried overnight under high vacuum at room temperature to afford 780 mg. of the title (S) isomer product as an amorphous solid, m.p. 103°–107° C. (dec.), [α]$_D$=+52.5 (c=0.55, methanol).

Analysis calc'd. for $C_{13}H_{14}F_3NO_5S \cdot 0.42\ H_2O$: C, 43.28; H, 4.14; N, 3.88; F, 15.80; S, 8.89; SH, 9.17 Found: C, 43.51; H, 4.40; N, 3.65; F, 15.63; S, 8.90; SH, 9.67.

EXAMPLE 46

(R)-3-Hydroxy-N-[3,3,3-trifluoro-2-(mercaptomethyl)-1-oxopropyl]-L-tyrosine

Concentrated ammonium hydroxide (2.6 mL) was added to a suspension of (R)-3-hydroxy-N-[2-[(acetylthio)methyl]-3,3,3-trifluoro-1-oxopropyl]-L-tyrosine (1.5 g., 3.8 mmol.), from Example 45(a), in deoxygenated water (2.6 mL) at room temperature. After stirring for one minute, saturated potassium bisulfate solution was added until a pH of about 1.5 was attained. The acidic mixture was extracted with ethyl acetate (2×125 mL) and the combined organic layers were washed with brine, dried (MgSO4), and concentrated. The residue was chromatographed on a 5×15 cm silica gel column using ethyl acetate:hexane:acetic acid, 55:45:2 as the mobile phase. The pure fractions were concentrated and coevaporated from hexane to provide a solid which was triturated with hexane and recrystallized from isopropanol/hexane. The crystalline solid was crushed to a fine powder and stirred in heptane for 3 hours to remove trapped isopropanol. The material was filtered, washed with hexane, and dried at 95° C. under high vacuum for 24 hours to afford 586 mg. of the title (R) isomer product as a white powder; m.p. 176°–177° C., [α]$_D$=+2.5° (c=0.32, methanol).

Analysis calc'd. for $C_{13}H_{14}F_3NO_5S \cdot 0.16\ H_2O$: C, 43.85; H, 4.05; N, 3.93; F, 16.00; S, 9.00; SH, 9.29 Found: C, 43.99; H, 4.22; N, 3.79; F, 15.60; S, 8.87; SH, 10.52.

EXAMPLE 47

(S,S)-α-[[3,3,3-Trifluoro-2-(mercaptomethyl)-1-oxopropyl]amino]cyclohexanepropanoic acid a)
N-[2-[(Acetylthio)methyl]-3,3,3-trifluoro-1-oxopropyl]-L-cyclohexylalanine Bis(trimethylsilyl)trifluoroacetamide (12.2 mL, 45.6 mmol.) was added to a suspension of L-cyclohexylalanine (2.6 g., 15.2 mmol) in 35 mL of acetonitrile at 0°. The suspension was stirred for 6 hours at room temperature. A significant amount of solid remained. After cooling the reaction mixture to 0° C., 2-trifluoromethyl-3-acetylthiopropionyl chloride (3.56 g., 15.2 mmol) was added dropwise as a solution in 10 mL of acetonitrile. After stirring for 24 hours at room temperature, the reaction mixture was a clear yellow solution. The reaction mixture was partitioned between ethyl acetate (150 mL) and 1N HCl (150 mL). The aqueous layer was extracted with an additional 150 mL of ethyl acetate. The combined organic layers were washed with water (2×400 mL) and brine (200 mL), dried (MgSO4), and concentrated to an oily residue. After two chromatographies and several recrystallizations 1.7 g. of (R)-N-[2-[(acetylthio)methyl]-3,3,3-trifluoro-1-oxopropyl]-L-cyclohexylalanine, m.p. 142°–145° C., [α]$_D$=−135.1° (c=0.37, methanol) were isolated and 2.19 g. of (S)-N-[2-[(acetylthio)methyl]-3,3,3-trifluoro-1-oxopropyl]-L-cyclohexylalanine, m.p. 106°–109° C., [α]$_D$=+97.2° (c=0.36, methanol) were isolated.

b)
(S,S)-α-[[3,3,3-Trifluoro-2-(mercaptomethyl)-1-oxopropyl]amino]cyclohexanepropanoic acid Concentrated ammonium hydroxide (3.1 mL) was added to a suspension of the title (S) isomer product from part (a) (1.734 g., 4.69 mmol.) in deoxygenated water (3.1 mL) at room temperature. Dissolution occurred almost immediately and the reaction mixture was stirred for 10 minutes at room temperature. The pH was adjusted to 1.5 with saturated potassium bisulfate solution and the mixture was extracted with ethyl acetate (200 mL). The organic layer was washed with brine, dried (MgSO4), and concentrated to a residue which was chromatographed on a 5×15 cm silica gel column. Elution with hexane: ethyl acetate:acetic acid, 80:20:2, concentration of the pure fractions, and co-evaporation from heptane afforded a white solid which was triturated with hexane. This solid was dried under high vacuum for 18 hours to afford 1.28 g. of the title (S,S) isomer product; m.p. 141°–143° C., $[\alpha]_D = +13.6°$ (c=0.85, methanol).

Analysis calc'd. for $C_{13}H_{20}F_3NO_3S$: C, 47.70; H, 6.16; N, 4.28; F, 17.41; S, 9.79; SH, 10.10 Found: C, 47.61; H, 6.15; N, 4.12; F, 17.24; S, 9.49; SH, 11.77.

EXAMPLE 48

(S,R)-α-[[3,3,3-Trifluoro-2-(mercaptomethyl)-1-oxo-propyl]amino]cyclohexanepropanoic acid Concentrated ammonium hydroxide (2.6 mL) was added to a suspension of (R)-N-[2-[(acetylthio)methyl]-3,3,3-trifluoro-1-oxopropyl]-L-cyclohexylalanine (1.7 g.) prepared as described in Example 47(a) in 10.5 mL of deoxygenated water at room temperature. Dissolution occurred almost immediately and the resulting solution was stirred for 5 minutes. At this time, the reaction mixture was acidified to pH 1.5 with saturated potassium bisulfate solution. The resulting suspension was extracted with ethyl acetate (about 250 mL). The organic layer was washed with brine, dried (MgSO4), and concentrated to an off-white solid. The material was chromatographed on a 2.5×20 cm silica gel column, using ethyl acetate:hexane:acetic acid, 80:20:2 as the mobile phase. Concentration of the pure fractions, co-evaporation from heptane and trituration with hexane afforded 858 mg. of the title (S,R) isomer as a white solid, m.p. 116°–118° C., $[\alpha]_D = -47.2°$ (c=0.65, methanol).

Analysis calc'd. for $C_{13}H_{20}F_3NO_3S$: C, 47.69; H, 6.16; N, 4.28; F, 17.41; S, 9.79; SH, 10.10 Found: C, 47.89, H, 6.29; N, 4.15; F, 16.76; S, 9.66; SH, 10.30.

EXAMPLE 49

(R)-N-[2-[(Acetylthio)methyl]-3,3,3-trifluoro-1-oxo-propyl]-L-tyrosine

A suspension of L-tyrosine (2.72 g., 15 mmol) in 50 mL of dry acetonitrile under argon was cooled to 0°–5° C. and bis(trimethylsilyl)trifluoroacetamide (12 mL, 45 mmol.) was added. The reaction mixture was allowed to stir and gradually warmed to room temperature. After 2 hours, 3 mL of dimethylformamide was added and allowed to stir overnight at room temperature. Since the reaction was still a light suspension, another 2 mL of dimethylformamide was added and after stirring for 2 hours at room temperature, 3 mL of bis(trimethylsilyl)-trifluoroacetamide was added which resulted in a clear solution in 2.5 hours. The reaction mixture was cooled to 0°–5° C. and 2-trifluoro-3-acetylthiopropionyl chloride (3.52 g., 15 mmol.) dissolved in 7 mL of acetonitrile was added dropwise and the mixture gradually warmed to room temperature. The reaction mixture was evaporated to a yellow syrupy residue, partitioned between ethyl acetate (100 mL) and water (100 mL). The aqueous layer was further extracted with additional ethyl acetate (4×75 mL), and the combined ethyl acetate extract was washed with brine (75 mL), dried (MgSO4), and evaporated to afford 10.5 g. of a yellow solid residue. This was combined with 2.5 g. of additional crude material prepared in another run. Flash chromatography of this 13 g. of crude material on silica gel (120:1 silica gel to compound) using ethyl acetate: hexanes: acetic acid, 100:100:1 as the eluent gave 2.29 g. of the faster eluting diastereomer (isomer A), 2.31 g. of a mixture of both diastereomers, and 1.88 g. of the slower eluting diastereomer (isomer B). The 2.29 g. portion was triturated with ethyl acetate:hexanes (1:1) to give 1.25 g. of pure isomer A and 0.83 g. of mother liquor containing both isomers. Similar treatment of the 1.88 g. material with ethyl acetate:hexanes (1:2) gave 1.2 g. of pure isomer B and 0.38 g. of mother liquor which contained predominately isomer B. Crystallization of the 2.31 g. fraction from ethyl acetate:hexanes (1:1) afforded 0.8 g. of pure isomer A and 1.5 g. of the mixed isomers A and B. The combined mixed fractions, 2.71 g., were rechromatographed twice using the same conditions to give 0.41 g. of pure isomer A and 1.14 g. of pure isomer B. The 0.8 g., 1.25 g., and 0.41 g. portions of pure isomer A were combined and first triturated with hexanes containing a few drops of ethyl acetate and then recrystallized from ethyl acetate:hexanes (1:1) to give 1.8 g. of the title (R) isomer product as a white crystalline solid; m.p. 202°–204° C., $[\alpha]_D = -85.7°$ (c=1.0, methanol).

Analysis calc'd. for $C_{15}H_{16}F_3NO_5S$: C, 47.49; H, 4.25; N, 3.69; F, 15.02; S, 8.45 Found: C, 47.55; H, 4.16; N, 3.62; F, 14.70 S, 8.25.

EXAMPLE 50

(S)-N-[2-[(Acetylthio)methyl]-3,3,3-trifluoro-1-oxo-propyl]-L-tyrosine

The 1.2 g. and 1.14 g. portions of pure isomer B from Example 49 were combined and triturated with hexane containing a few drops of ethyl acetate to give 2.2 g. of the title (S) isomer product as a white solid, m.p. 170°–173° C., $[\alpha]_D = +11.8°$ (c=1.0, methanol).

Analysis calc'd. for $C_{15}H_{16}F_3NO_5S$: C, 47.49; H, 4.25; N, 3.69; F, 15.02; S, 8.45 Found: C, 47.49; H, 4.22; N, 3.67; F, 14.67; S, 8.27.

EXAMPLE 51

(R)-N-[3,3,3-Trifluoro-2-(mercaptomethyl)-1-oxo-propyl]-L-tyrosine

A suspension of the (R) isomer product of Example 49 (1.66 g., 4.4 mmol.) in 2.8 mL of concentrated ammonium hydroxide and 6.2 mL of water was stirred at room temperature under argon for 7 minutes. The resulting clear solution was acidified with 5% potassium bisulfate solution to pH 1.5 and extracted with 75 mL of ethyl acetate followed by an additional 3×50 mL portions of ethyl acetate. The combined ethyl acetate extract was washed with brine (75 mL), dried (MgSO4), and evaporated to yield 1.48 g. of a white crystalline solid. Flash chromatographic purification of this crude product on silica gel (240:1 silica gel to compound) using ethyl acetate:hexanes: acetic acid, 100:100:1 as the eluent gave 1.32 g. of the title (R) isomer product as a white crystalline solid, m.p. 204°–206° C., $[\alpha]_D = +5.2°$ (c=1.0, methanol).

Analysis calc'd. for $C_{13}H_{14}F_3NO_4S$: C, 46.29; H, 4.18; N, 4.15; F, 16.90 S, 9.50; SH, 9.80 Found: C, 46.32; H, 4.02; N, 4.04; F, 16.60; S, 9.52; SH, 9.86.

EXAMPLE 52

(S)-N-[3,3,3-Trifluoro-2-(mercaptomethyl)-1-oxo-propyl]-L-tyrosine

A suspension of the (S) isomer product of Example 50 (2.05 g., 5.4 mmol) in 3.5 mL of concentrated ammonium hydroxide and 7.6 mL of water was stirred at room temperature under argon for 7 minutes. The clear solution was acidified with 150 mL of 5% potassium bisulfate solution and extracted with 75 mL of ethyl acetate followed by an additional 4×50 mL of ethyl acetate. The combined ethyl acetate extract was washed with brine (100 mL), dried (MgSO$_4$) and evaporated under reduced pressure to afford 1.95 g. of an off-white solid. Flash chromatography on 400 g. of silica gel using ethyl acetate:hexanes:acetic acid, 100:100:1 as the eluent yielded 1.56 g. of the title (S) isomer as a white crystalline solid; m.p. 184°–187° C., $[\alpha]_D = +59.0°$ (c=1.0, methanol).

Analysis calc'd. for $C_{13}H_{14}F_3NO_4S$: C, 46.29; H, 4.18; N, 4.15; F, 16.90; S, 9.50; SH, 9.80 Found: C, 46.38; H, 4.13; N, 4.12; F, 16.73; S, 9.37; SH, 9.44.

EXAMPLE 53

(S,S)-3,3,3-Trifluoro-2-(mercaptomethyl)-N-[2-(1 H-indol-3-yl)-1-(1 H-tetrazol-5-yl)ethyl]propanamide a) (S)-α-(1 H-Tetrazol-5-yl)-1 H-indol-3-ethanamine, hydrochloride To a solution of N-[(1,1-dimethylethoxy)carbonyl]-L-tryptophan (7.74 g., 25.42 mmol.) in methylene chloride (150 mL) at −20° C. under argon was added N-methylmorpholine (2.79 mL, 25.42 mmol.) followed by isobutylchloroformate (3.31 mL, 25.42 mmol.). The resuting suspension was stirred at −20° C. for 15 minutes at which time 5.6M NH$_3$/methanol (45 mL, 252 mmol) was added. After 30 minutes at −20° C., the reaction was quenched with water and warmed to room temperature. The layers were separated and the aqueous layer extracted twice with methylene chloride. The combined organic extracts were dried (MgSO$_4$) and evaporated to give 8.0 g. of a white solid. Recrystallization from ethyl acetate/hexanes gave 6.6 g. of N-[(1,1-dimethylethoxy)carbonyl]-L-tryptophanamide.

To a solution of triethylamine (10.5 mL, 75.16 mmol) in benzene (40 mL) at 10° C. under argon was added chlorosulfonyl methylcarbamate (6.5 g., 37.58 mmol) dissolved in benzene (70 mL) over 30 minutes. The reaction mixture was stirred an additional 30 minutes at room temperature at which point N-[(1,1-dimethylethoxy)carbonyl]-L-tryptophanamide (5.7 g., 18.79 mmol) dissolved in anhydrous tetrahydrofuran (100 mL) was added over 10 minutes. The resulting mixture was stirred for one hour and then poured onto a flash chromatography column (50 mm×6 inches, elution with 60:40 hexanes:ethyl acetate) to give 4.22 g. of N-[(1,1-dimethylethoxy)carbonyl]-L-tryptophanylnitrile as a white solid. TLC $R_f$=0.47 (1:1, ethyl acetate:hexanes), $[\alpha]_D = -35.8°$ (c=0.57, methanol).

A solution of this nitrile compound (2.42 g., 8.48 mmol.) and tributyltin azide (4.25 g., 12.72 mmol. in xylenes (20 mL) was stirred at 90° C. for one hour. The mixture was cooled to room temperature and poured directly onto a flash chromatography column (50 mm×8 inches, elution with 2 L 60:40 hexanes:ethyl acetate +2% acetic acid and 1 L 3:1 ethyl acetate:hexanes +2% acetic acid) to give 1.91 g. of (S-[2-(1 H-indol-3-yl)-1-(1 H-tetrazol-5-yl)ethyl]carbamic acid, 1,1-dimethylethyl ester as a white solid. TLC $R_f$=0.09 (60:40 hexanes:ethyl acetate +2% acetic acid), $[\alpha]_D = +2.23°$ (c=0.71, methanol).

Ethyl acetate (30 mL) was saturated with HCl gas at 0° C. at which point anisole (7.4 mL) was added followed by (S)-[2-(1H-indol-3-yl)-1-(1 H-tetrazol-5-yl)ethyl]carbamic acid, 1,1-dimethylethyl ester (1.24 g., 3.77 mmol.) dissolved in ethyl acetate (7 mL). The resulting solution was stirred at 0° for one hour at which time TLC showed that no starting material remained. The reaction mixture was evaporated and chased with methylene chloride and ether and finally pumped to 0.95 g. of (S)-α-(1 H-tetrazol-5-yl)-1 H-indol-3-ethanamine, hydrochloride as a light brown solid.

b) (2S)-Trifluoromethyl-3-acetylthiopropionic acid, ephedrine salt

2-Trifluoromethyl-3-acetylthiopropionic acid (7.18 g., 33.2 mmol) in ether (100 mL) was treated with (1S,2R)-(+)-ephedrine (2.73 g., 16.6 mmol) in ether (100 mL) and allowed to sit for 18 hours. The reaction mixture was then filtered to give 5.37 g. of a solid which was recrystallized from ethyl acetate (4×40 mL) to give 3.47 g. of (2S)-trifluoromethyl-3-acetylthiopropionic acid, ephedrine salt, m.p. 139°–140° C., $[\alpha]_D = +100.0°$ (C=1.0, methanol).

c) (S,S)-2-[(Acetylthio)methyl]-3,3,3-trifluoro-N-[2-(1 H-indol-3-yl)-1-(1 H-tetrazol-5-yl)ethyl]propanamide The ephedrine salt product of part (b) (2.2 g., 5.74 mmol) was shaken in a separatory funnel with ethyl ether (50 mL) and water (50 mL) containing 1N HCl (5.74 mL). The organic layer was separated, dried (MgSO$_4$), evaporated, and azeotroped with methylene chloride. The resulting free carboxylic acid was dissolved in methylene chloride (14 mL) to which was added oxalyl chloride (0.5 ml., 5.74 mmol) followed by careful dropwise addition of dimethylformamide (0.05 mL). The resulting mixture was stirred at room temperature for 2 hours. At the same time, to a suspension of the title A product (1.73 g., 5.74 mmol) in acetonitrile (30 mL) at 0° C. under argon was added bis(trimethlsilyl)trifluoroacetamide (6.3 mL, 24.12 mmol) and the resulting cloudy solution was stirred at room temperature for 2 hours. This solution was then cooled to −25° C. at which time the above (2S)-trifluoromethyl-3-acetylthiopropionyl chloride was added dropwise over 15 minutes. After stirring the light-yellow solution for 2 hours at −25° C. to −15° C., the reaction was quenched by pouring into water (75 mL) and extracted with ethyl acetate (2×75 mL). The combined organic extracts were washed with brine (75 mL), dried (Na$_2$SO$_4$), and evaporated to a solid. Flash chromatography (50 mm×8 inch column, eluting with 2 L 1:1 hexane:ethyl acetate +1% acetic acid, 1 L 3:1 ethyl acetate:hexanes +2% acetic acid 1 L 4:1 ethyl acetate:hexanes +2% acetic acid 1 L 9:1 ethyl acetate:hexanes +2% acetic acid) gave after recrystallization from ethyl acetate/hexanes, 1.52 g. of the title C (S,S) isomer product as a white solid, m.p. 208°–213° C. (dec.), TLC $R_f$=0.13 (60:40 hexanes:ethyl acetate +2% acetic acid), $[\alpha]_D = -163.8°$ (c=0.53, methanol).

d)

(S,S)-3,3,3-Trifluoro-2-(mercaptomethy)-N-[2-(1H-indol-3-yl)-1-(1 H-tetrazol-5-yl)ethyl]propanamide To a suspension of title C product (1.14 g., 2.67 mmol.) in degassed water (5.3 mL) at room temperature under argon was added a mixture of concentrated NH$_4$OH (1.76 mL) and water (1.76 mL). After 2 minutes, the reaction was quenched with saturated potassium bisulfate (pH 1.5) and the resulting solid filtered off and purified by trituration with a mixture of ethyl acetate/ethyl ether/hexanes to give 0.73 g. of the (S,S)

isomer product as a white solid, m.p. 218°-223° C. (dec.), TLC R$_f$=0.13 (60:40 hexanes/ethyl acetate +2% acetic acid) [α]$_D$= +54.8° (c=0.54, methanol).

Analysis calc'd. for C$_{15}$H$_{15}$F$_3$N$_6$OS: C, 46.87; H, 3.93; N, 21.86; F, 14.83; S, 8.34; SH 8.60 Found: C, 47,22; H, 3.80; N, 21.71; F, 14.99; S, 8.05; SH, 12.35.

EXAMPLE 54

(S,R)-3,3,3-Trifluoro-2-(mercaptomethyl)-N-[2-(1 H-indol-3-yl)-1-(1H-tetrazol-5-yl)ethyl]propanamide a) (2R)-Trifluoromethyl-3-acetylthiopropionic acid, ephedrine salt

The filtrate obtained in Example 53(b) was evaporated, treated with aqueous HCl, and then extracted into ethyl acetate, dried, and evaporated to give 3.8 g. of an oil. This oil was dissolved in ether (40 mL) and combined with (1R,2S)-(−)-ephedrine (2.9 g., 17.6 mmol) dissolved in ether (40 mL) and allowed to sit for 16 hours. The solid was filtered off and recrystallized from ethyl acetate (2×40 mL) to give 4.0 g. (2R)-trifluoromethyl-3-acetylthiopropionic acid, ephedrine salt, m.p. 138°-139° C., [α]$_D$= −100.3° (c=1.0, methanol).

b) (S,R)-2-[(Acetylthio)methyl]-3,3,3-trifluoro-N-[2-( 1 H-indol-3-yl)-1-(1 H-tetrazol-5-yl)ethyl]propanamide The ephedrine salt product of title A (1.53 g., 4.0 mmol) was shaken in a separatory funnel with ethyl ether (50 mL) and water (50 mL) containing 1N HCl (4.0 mL). The organic layer was separated, dried (MgSO$_4$), evaporated and azeotroped with methylene chloride. The resulting free carboxylic acid was dissolved in methylene chloride (10 mL) to which was added oxalyl chloride (0.35 mL, 4.0 mmol) followed by the careful dropwise addition of dimethylformamide (0,035 mL). The resulting mixture was stirred at room temperature for 2 hours. At the same time, to a suspension of (S)-α-(1 H-tetrazol-5-yl)-1 H-indole-3-ethanamine, hydrochloride (1.73 g., 5.74 mmol) in acetonitrile (21 mL) at 0° C. under argon was added bis(trimethylsilyl)trifluoroacetamide (4.4 mL, 16.8 mmol) and the resulting cloudy solution was stirred at room temperature for 2 hours. This solution was then cooled to −25° C. and the acid chloride solution was added dropwise over 15 minutes. After stirring the light-yellow solution for 2 hours at −25° to −15° C., the reation was quenched by pouring into water (50 mL) and extracted with ethyl acetate (2×50 mL). The combined organic extracts were washed with brine (50 mL), dried (Na$_2$SO$_4$), and evaporated to a solid. Flash chromatography (50 mm×8 inch eluting with 2 L 1:1 hexanes:ethyl acetate +1% acetic acid, 1L 3:1 ethyl acetate:hexanes +2% acetic acid) gave, after recrystallization from ethyl acetate/hexanes, 0.68 g. of the title B product as a white solid. The mother liquors were evaporated and re-chromatographed (25 mm×6 inch, eluting with 2 L 1:1 hexanes: ethyl acetate +1% acetic acid) to give, after recrystallization from ethyl acetate/hexanes, an additional 0.26 g. of white solid for an overall yield of 0.96 g. of the title B product, m.p. 206°-213° C., (dec.), TLC R$_f$=0.23 (60:40 hexanes:ethyl acetate +2% acetic acid) [α]$_D$= −93.3° (c=0.52, methanol).

c) (S,R)-3,3,3-Trifluoro-2-(mercaptomethyl)-N-[2(1 H-indol-3-yl)-1-(1 H-tetrazol-5-yl)ethyl]propanamide To a suspension of the (S,R) title B product (0.9 g., 2.1 mmol) in degassed water (4.2 mL) at room temperature under argon was added a mixture of concentrated NH$_4$OH (1.39 mL) and water (1.39 mL). After 2 minutes, the reaction was quenched with saturated potassium bisulfate (pH 1.5) and the resulting mixture extracted into ethyl acetate. The organic layer was washed with water and brine, dried, and evaporated to give a solid which was purified by flash chromatography (50 mm×7 inch eluting with 1:1 ethyl acetate: hexanes +1% acetic acid). The resulting material was recrystallized from ethyl acetate/hexane to give 0.59 g. of the title (S,R) product as a white solid, m.p. 206°-213° (dec.), TLC R$_f$=0.11 (60:40 hexanes:ethyl acetate +2% acetic acid), [α]$_D$= −38.6° (c=0.42, methanol).

Analysis calc'd. for C$_{15}$H$_{15}$F$_3$N$_6$OS·0.1 H$_2$O: C, 46.66; H, 3.97; N, 21.76; F, 14.76; S, 8.30; SH, 8.56 Found: C, 46.93; H, 3.80; N, 21.38; F, 15.06; S, 8.38; SH, 15.40.

EXAMPLE 55

(S)-N-[4,4,4-Trifluoro-2-(mercaptomethyl)-1-oxobutyl]-L-leucine a) 2-[[(Phenylmethyl)thio]methyl]-4,4,4-trifluorobutyric acid

To a solution of lithium diisopropylamide [prepared using freshly distilled diisopropylamine (4.47 g., 44.4 mmol) and n-butyl lithium/hexane (18 mL, 45 mmol, 2.5M)]in dry tetrahydrofuran (35 mL) was added a solution of 4,4,4-trifluorobutyric acid (3.0 g., 21.0 mmol) in tetrahydrofuran (25 mL). After stirring at 0° C. for 1.5 hours, the solution was cooled to −78° C. and treated with a solution of benzyl bromomethyl thioether in tetrahydrofuran (10 mL). The solution was allowed to stir overnight as the temperature rose to ambient. Volatiles were removed in vacuo and the residue was dissolved in ethyl acetate and extracted with 1N sodium hydroxide (50 mL) and water (2 x 20 mL). The combined basic extracts were acidified with concentrated hydrochloric acid (8 mL) and extracted with ethyl acetate (2×100 mL). The organic extracts were washed with water and brine, combined, dried (MgSO$_4$), and concentrated in vacuo to give 3.82 g. of an oil. Flash chromatography on 350 mL of silica gel and elution with ethyl acetate:hexanes: acetic acid, 50:100:1 gave 1.36 g. of the title A product, TLC R$_f$=0.38 (ethyl acetate:hexanes:acetic acid, 50:50:1).

b) N-[2-[[(Phenylmethyl)thio]methyl]-4,4-trifluoro-1-oxobutyl]-L-leucine

The acid product of part (a) (2.26 g., 8.1 mmol) was converted to the acid chloride by heating with thionyl chloride (8 mL) at 90° C. for 2.5 hours, removing excess thionyl chloride by distillation, and pumping the resulting residue on high vacuum at 70° C. for several hours. This acid chloride was dissolved in dry acetonitrile (5 mL) and added to an ice-cooled acetonitrile solution of L-leucine/bis(trimethylsilyl)trifluoroacetamide [prepared from L-leucine (1.12 g., 8.5 mmol) and bis(trimethylsilyl)trifluoroacetamide (4.85 mL, 4.7 g., 18.27 mmol) in 45 mL of dry acetonitrile at 0° to ambient temperature overnight]. After stirring for 5 hours, volatiles were removed in vacuo and the residue was dissolved in ethyl acetate, washed with 5% potassium bisulfate, water, and brine. The dried (MgSO$_4$) organic solution was concentrated in vacuo to give 4.5 g. of an oil. Flash chromatography on 500 mL of silica gel and elution with ethyl acetate:hexanes:acetic acid (80:120:0.5) gave 2.56 g. of product containing some by-product.

HPLC was performed using 400 mg. sample (2.85 g. total) injections on a 30×500 mm YMC S-10 column under isocratic conditions of 70:30 (B-90/10 methanol/water—0.1% trifluoroacetic acid:A-10/90 methanol/water-0.1% trifluoroacetic acid) at a flow rate of 50 mL/min., the pooled fractions containing the desired product were concentrated in vacuo to remove methanol and the resulting aqueous concentrate was extracted with ethyl acetate (3 x). The organic fractions were washed with water and brine, combined, dried ($MgSO_4$), and concentrated in vacuo to give 2.43 g. of the title B product.

c)
(S)-N-[4,4,4-Trifluoro-2-(mercaptomethyl)-1-oxobutyl]-L-leucine

To liquid ammonia (100 mL) at $-78°$ C. were added small sodium chips (527 mg., 22.9 mg. atom). After 10 minutes (blue color formed immediately), a solution of the title B product (1.53 g., 3.9 mmol) in dry tetrahydrofuran (3.9 mL) was added followed 10 minutes later by solid ammonium chloride (5 g., 94 mmol) to quench the reaction which was now allowed to warm to $-33°$ C. (disappearance of blue color). Excess ammonia was evaporated (with argon flow) and the residue was partitioned between ethyl acetate and 10% potassium bisulfate. The organic layer was separated, washed with water and brine, and dried ($MgSO_4$), to give 1.2 g., of material (combined with another run for a total of 1.88 g.).

The diastereomers were separated by flash chromatography on 500 mL of silica gel, eluting with ethyl acetate/hexane/acetic acid (60:140:0.5 then 80:100:0.5). Rechromatography of various mixed fractions and hexane (ethyl acetate) trituration affords 700 mg. of the title (S) isomer product as a white solid, m.p. 102°-105° C., TLC $R_f=0.29$ (ethyl acetate:hexane:acetic acid, 100:100:1) $[\alpha]_D=-42.6°$ (c=0.97, methanol).

Analysis calc'd. for $C_{11}H_{18}F_3NO_3S$: C, 43.85; H, 6.02; N, 4.65; F, 18.91; S, 10.64; SH, 10.97 Found: C, 43.72; H, 5.62; N, 4.70; F, 18.94; S, 10.45; SH, 11.94.

EXAMPLE 56

(R)-N-[4,4,4-Trifluoro-2-(mercaptomethyl)-1-oxobutyl]-L-leucine

Following the procedure of Example 55, further work up of appropriate chromatography fractions afforded 578 mg. of the titled product which was the slower moving isomer as a white solid, m.p. 78°-81° C. TLC $R_f=0.23$ (ethyl acetate hexane:acetic acid, 100:100:1). $[\alpha]_D=-9.6°$ (c=0.53, methanol).

Analysis calc'd. for $C_{11}H_{18}F_3NO_3S$: C, 43.85; H, 6.02; N, 4.65; F, 18.91; S, 10.64; SH, 12.64 Found: C, 43.84; H, 6.04; N, 4.62; F, 18.93; S, 10.48; SH, 12.64.

EXAMPLE 57

(S,R)-α-[[3,3,3-Trifluoro-2-(mercaptomethyl)-1-oxopropyl]amino]-2-benzofuranpropanoic acid a) Benzofuran-2-methanol Benzofuran-2-carboxylic acid (4.59 g., 28.3 mmol) as a solution in dry ethyl ether (100 mL) was added dropwise over 15 minutes to a suspension of lithium aluminum hydride (4.3 g., 113 mmol) in ethyl ether (180 mL) at 0° C. The reaction mixture was stirred for 2 hours while warming to room temperature. After recooling to 0° C., 4.3 mL of water was added with extreme caution. Sodium hydroxide (4.3 mL, 15% in water) was then added followed by an additional 12.9 mL of water. Magnesium sulfate (about 10 g.) was added and the thick white suspension was stirred briskly for about 30 minutes. The suspension was filtered through silica gel and the filter cake was washed thoroughly with ethyl ether. The filtrate was concentrated and dried under high vacuum to afford 4.15 g. of the title A product as a light yellow oil.

b) 2-(Bromomethyl)benzofuran

Triphenylphosphine (10.83 g., 41.3 mmol) was added to a solution of the title A product (4.08 g., 27.5 mmol) and carbon tetrabromide (13.93 g., 42 mmol) in dimethylformamide (85 mL) at 0° C. After stirring for 30 minutes, saturated sodium bicarbonate solution (50 mL) and water (50 mL) were added. The resulting mixture was partitioned between hexane and water. The organic layer was washed with water and brine, dried ($MgSO_4$), and concentrated to a yellow liquid. This material was chromatographed on a 5×20 cm silica gel column using hexane as the mobile phase. The pure fractions were concentrated to afford 4.32 g. of (2-bromomethyl)benzofuran as a white crystalline solid.

c)
[3aS-[3α,6α,7β]]-1-[[[Bis(methylthio)methylene]amino]acetyl]hexahydro-3 H-3a,6-methano-2,1-benzisothiazole, 2,2-dioxide Carbon disulfide (6.3 mL, 105 mmol) was added to a mixture of glycine methyl ester hydrochloride (12.5 g., 100 mmol) in chloroform (100 mL) at room temperature. Triethylamine (14.6 mL, 105 mmol) was then added and the reaction temperature rose from 22° C. to 37° C. After stirring for one hour, methyl iodide (6.8 mL, 110 mmol) was added dropwise and the reaction mixture was refluxed for one hour. After cooling to room temperature, the reaction mixture was washed with water (2×50 mL) and evaporated. The residue was taken up in ethyl ether (60 mL) and washed with water (2×20 mL). Drying over sodium sulfate and concentration afforded 9 g. of the intermediate monomethylbisthiomethylene glycinate as an oil.

A mixture of this oil, pulverized potassium carbonate (10.3 g., 75 mmol) and methyl iodide (3.4 mL, 55 mmol) in acetone (30 mL) was refluxed under argon for 2 hours. An additional amount of methyl iodide (0.5 mL, 8.1 mmol) was added and the reaction mixture was refluxed for one more hour. After cooling, the mixture was filtered and the filter cake was washed with acetone. The filtrate was concentrated and the residue was dissolved in ethyl ether (30 mL). This solution was washed with water (2×10 mL), dried over sodium sulfate and concentrated to afford 9.12 g. of methyl N-[bis(methylthio)methylene]glycinate as a yellow oil.

A solution of trimethylaluminum (11.95 mL, 23.9 mmol, 2M in toluene) was added dropwise over 30 minutes to a solution of D-2,10-camphorsultam in toluene (120 mL) at room temperature. After stirring for 15 minutes, methyl N-[bis(methylthio)methylene]glycinate (4.2 g., 19.8 mmol) was added as a solution in toluene (80 mL) dropwise over 30 minutes. The reaction mixture was then heated to 50° C. for 24 hours. After cooling to room temperature, 7 mL of water were added with extreme caution. After the addition of water was complete, magnesium sulfate was added. After stirring for 15 minutes, the suspension was filtered through Celite and the filtrate was concentrated to an orange oil. This residue was recrystallized from absolute ethanol to afford 5.86 g. of the title C product as colorless crystals, m.p. 106°-108° C.

d) [3aS-[3aα,6α,7β]-1-[3-(2-Benzofuranyl-2-[[bis(methyl-thio)methylene]amino]-1-oxopropyl]hexahydro-3 H-3a,6-methano-2,1-benzisothiazole, 2,2-dioxide A solution of the title C product (0.94 g., 2.5 mmol) in dry tetrahydrofuran (3.75 mL) was added to a solution of n-butyl lithium (0.92 mL, 2.3 mmol, 2.5M in hexane) in dry tetrahydrofuran (6.25 mL) at −78° C. over 10 minutes. The mixture was stirred one hour at −78° C., after which time 2-(bromomethyl)benzofuran (486 mg., 2.3 mmol) was added dropwise over 10 minutes as a solution in dry tetrahydrofuran (1.25 mL) and hexamethylphosphoric triamide (1.25 mL). Tetrabutylammoniumiodide (50 mg.) was then added and the reaction was stirred at −78° C. to −20° C. over 2 hours. Water was then added and the mixture was extracted with ethyl acetate (150 mL). The organic layer was washed with water (100 mL) and brine (100 mL), dried (MgSO$_4$), and concentrated to afford an oily residue which was crystallized from about 4 mL of absolute ethanol. The colorless crystals were filtered and washed with ethanol (10 mL) that had been cooled to −20° C. Drying under high vacuum afforded 1.08 g. of the title D product as a colorless crystalline solid, m.p. 145°-148° C., TLC R$_f$=0.18 (methylene chloride), [α]$_D$=−86.5° (c=0.40, chloroform).

e) [3aS-[3aα,6α,7β]]-1-[2-Amino-3-(2-benzofuranyl)-1-oxopropyl]hexahydro-3 H-3a,6-methano-2,1-benzisothiazide,2,2-dioxide A mixture of the title (D) product (1.05 g., 2.07 mmol), 0.5N HCl (11 mL, 5.5 mmol) and tetrahydrofuran (11 mL) was stirred at 40° C. for 18 hours. After basifying to pH 12 with 6N sodium hydroxide, the mixture was extracted with ethyl acetate. The organic layer was washed with brine, dried over sodium sulfate, and concentrated to an oily residue. The oil was dissolved in about 2.5 mL of ethyl acetate and hexane and was added until the solution became slightly turbid. Seed crystals were added and the mixture was allowed to crystallize. Filtration and drying under high vacuum afforded 0.71 g. of the title E compound as a colorless crystalline solid, m.p. 123°-125° C., TLC R$_f$=0.16 (ethyl acetate:hexane, 1:1), [α]$_D$=−52.8° (c=0.29, chloroform).

f) (S)-α-Amino-2-benzofuranpropanoic acid, hydrochloride

Lithium hydroxide monohydrate (336 mg., 8 mmol) was added as a solution in water (10 mL) to a solution of the title E product (0.71 g.) in tetrahydrofuran (20 mL) at room temperature. After stirring the biphasic reaction mixture for one hour, water (30 mL) was added and the mixture was extracted with methylene chloride (2×25 mL). After acidifying the aqueous layer to pH 1.5 with 1N HCl, the solvent was removed in vacuo to afford a white solid. This solid was loaded as a suspension in water onto an HP-20 column which was eluted with water (500 mL), 1:1 water:methanol (500 mL), and 2:3 water:methanol (250 mL). The product containing fractions were combined, reacidified to pH 1.5 with 1N HCl, and concentrated to afford 465 mg. of the title F product as a white powder, m.p. 190° C. (darkened), 225°-230° C. (dec.), TLC R$_f$=0.36 (butanol:acetic acid:water: ethyl acetate, 1:1:1:2), [α]$_D$=−9.5° C. (c=0.55, methanol).

g) (S,R)-α-[[3,3,3-Trifluoro-2-[(acetylthio)methyl]-1-oxo-propyl]amino]-2-benzofuranpropanoic acid The ephedrine salt product from Example 54(a) (393 mg., 1.03 mmol) was partitioned between ethyl ether (100 mL) and dilute HCl (1.03 mL of 1N HCl in 100 mL of water). The ether layer was washed with water (2×100 mL), dried (MgSO$_4$), and concentrated. The residue was evaporated from methylene chloride (2×20 mL). The free acid was dissolved in methylene chloride (3 mL) and oxalyl chloride (0.09 mL, 1.03 mmol) was added. Dimethylformamide (0.009 mL, 0.01 mmol) was added and the mixture was stirred at room temperature for 2 hours. Concurrently, bis(trimethylsilyl)trifluoroacetamide (771 mg., 3.0 mmol.) was added to a suspension of the title F product (275 mg., 1.0 mmol.) in acetonitrile (10 mL). While stirring for 2.5 hours, this suspension became a light yellow solution. This mixture was cooled to 0° C. and the above acid chloride solution was added in one portion. After warming to room temperature, the mixture was stirred for 18 hours. The reaction mixture was partitioned between ethyl acetate (75 mL) and 1 N HCl (75 mL). The aqueous layer was extracted with an additional 25 mL of ethyl acetate and the combined organic layers were washed with 1N HCl 50 mL) followed by brine (25 mL). The organic layer was then dried (MgSO$_4$), concentrated and co-evaporated from toluene (2×10 mL). The residue was chromatographed on a 2.5×20 cm silica gel column using hexane:ethyl acetate:acetic acid, 60:40:2 as the mobile phase. The pure fractions were concentrated and the residue was coevaporated with heptane to afford 259 mg. of a white solid which was recrystallized from ethyl acetate/hexane to give 224 mg. of the (S,R) title G product, m.p. 147°-149° C., TLC R$_f$=0.26 (ethyl acetate:hexane: acetic acid, 60:40:2).

h) (S,R)-α-[[3,3,3-Trifluoro-2-(mercaptomethyl)-1-oxo-propyl]amino]-2-benzofuranpropanoic acid Concentrated ammonium hydroxide (1 mL) was added to a suspension of the title G product (200 mg., 0.5 mmol) in water (4 mL). Dissolution occurred in one minute and the reaction was allowed to stir for a total of 2 minutes. At this time, the pH was adjusted to 1.5 with saturated potassium bisulfate solution and the mixture was extracted with ethyl acetate (2×30 mL). The combined organic layers were washed with brine (30 mL), dried (MgSO$_4$), and concentrated to a tan solid which was chromatographed on a 2.5×15 cm silica gel column using hexane:ethyl acetate:acetic acid, 60:40:1 as the mobile phase. The pure fractions were concentrated and coevaporated from heptane to give a white solid which was triturated with pentane to afford 161 mg. of the title (S,R) product as a white solid; m.p. 143°-145° C., TLC R$_f$=0.31 (ethyl acetate:hexane:acetic acid, 60:40:2), [α]$_D$=−2.4° C., (c=0.45, methanol).

Analysis calc'd. for $C_{15}H_{14}F_3NO_4S$: C,49.86; H, 3.91; N, 3.88; F, 15.77; S, 8.87; SH, 9.15 Found: C, 49.82; H, 4.12; N, 4.22; F, 15.90; S, 8.64; SH, 9.68.

EXAMPLE 58

(S,S)-α-[[3,3,3-Trifluoro-2-(mercaptomethyl)-1-oxo-propyl]amino]-2-benzofuranpropanoic acid a)

(S,S)-α-[[3,3,3-Trifluoro-2-[(acetylthio)methyl]-1-oxo-propyl]amino-2-benzofuranpropanoic acid The ephedrine salt product of Example 53(b) (425 mg., 1.22 mmol) was partitioned between ethyl ether (100 mL) and dilute HCl (1.22 mL of 1N HCl in 100 mL of water). The ether layer was washed with water (2×100 mL), dried (MgSO$_4$), and concentrated. The residue was coevaporated from methylene chloride (2×20 mL). The free acid was dissolved in methylene chloride (3 mL) and oxalyl chloride (0.107 mL, 1.22 mmol) was added. Dimethylformamide (0.011 mL, 0.012 mmol) was added and the mixture was stirred at room temperature for 2 hours. Concurrently bis (trimethylsilyl)trifluoroacetamide (0.75 mL, 2.8 mmol) was added to a suspension of the product from Example 57 (f) (465 mg.) in acetonitrile. While stirring for 2.5 hours, this suspension became a light yellow solution. This mixture was cooled to 0° C. and the above acid chloride solution was added in one portion. After warming to room temperature, the mixture was stirred for 18 hours. The reaction mixture was partitioned between ethyl acetate (75 mL) and 1N HCl (75 mL). The ethyl acetate layer was washed with 1N HCl (75 mL), water (75 mL), and brine (75 mL). The organic layer was then dried (MgSO$_4$), concentrated, and coevaporated from toluene (2×10 mL). The residue was chromatographed on a 2.5×20 cm silica gel column using 1 L hexane: ethyl acetate:acetic acid (70:30:2) and 1 L hexane:ethyl acetate:acetic acid (60:40:2) as the mobile phase. The pure fractions were concentrated and the residue coveaporated from heptane to afford 270 mg. of tan solid which was recrystallized from ethyl acetate/hexane. Filtration and washing with heptane afforded 203 mg. of the (S,S) title A compound as a white solid, m.p. 139°–140° C., TLC R$_f$=0.10 (ethyl acetate:hexane:acetic acid, 50:50:2).

b)

(S,S)-α-[[3,3,3-Trifluoro-2-(mercaptomethyl)-1-oxo-propyl]amino]-2-benzofuranpropanoic acid Concentrated ammonium hydroxide (0.9 mL) was added to a suspension of the title A product (180 mg., 0.45 mmol) in water (3.6 mL). Dissolution occurred in one minute and the reaction was allowed to stir a total of 2 minutes. At this time the pH was adjusted to about 1.5 with saturated potassium bisulfate solution and the mixture was extracted with ethyl acetate (50 mL). The organic layer was washed with brine (50 mL), dried (MgSO$_4$), and concentrated. The residue was combined with that from another run (18 mg.) and chromatographed on a 2.5×15 cm silica gel column using hexane:ethyl acetate:acetic acid, 60:40:1 as the mobile phase. The pure fractions were concentrated and coevaporated with heptane to a white solid which was triturated with pentane to afford 146 mg. of the (S,S) title product as a white solid, m.p. 141°–142° C., TLC R$_f$=0.30 (ethyl acetate:hexane:acetic acid, 60:40:2), [α]$_D$=+45.7° (c=0.37, methanol).

Analysis calc'd. for C$_{15}$H$_{14}$F$_3$NO$_4$S: C, 49.86; H, 3.91; N, 3.88; F, 15.77; S, 8.87; SH, 9.15 Found: C, 49.80; H, 3.90; N, 3.88; F, 15.99; S, 8.96; SH, 9.24.

EXAMPLE 59

(S)-1-[N-[3,3,3-Trifluoro-2-(mercaptomethyl)-1-oxo-propyl]-L-alanyl]-L-proline a)

(S)-1-[N-[3,3,3-Trifluoro-2-[(acetylthio)methyl]-1-oxo-propyl]-L-alanyl]-L-proline The ephedrine salt product of Example 53(b) (1.64 g. 4.3 mmol) was partitioned between ethyl acetate and aqueous HCl (6 mmol). The organic layer was washed with water and brine, dried (MgSO$_4$), and concentrated in vacuo to give 0.94 g. of free acid. The material was dissolved in methylene chloride (10 mL) at room temperature and treated with oxalyl chloride (400 μL, 573 mg., 4.51 mmol) and one drop of dimethylformamide. After 1.5 hours, this solution was added to a solution of L-alanyl-L-proline/bis(trimethylsilyl) trifluoroacetamide in acetonitrile [prepared from L-alanyl-L-proline, tosylate (1.54 g., 4.3 mmol), diisopropylethyl amine (0.75 mL, 554 mg., 4.3 mmol), and bis(trimethylsilyl)trifluoroacetamide (2.3 mL, 2.21 g., 8.6 mmol) in 15 mL of acetonitrile, stirred for two hours at 0° C. to room temperature to give a homogeneous solution] and allowed to stir overnight. Volatiles were removed in vacuo and the residue, dissolved in ethyl acetate, was washed with 10% potassium bisulfate, water, and brine. The organic fraction was dried (MgSO$_4$) and concentrated in vacuo to give an oil. Flash chromatography on 250 mL of silica gel eluting with ethyl acetate: hexane:methanol:acetic acid (10:6:2:0.2) gave 1.2 g. of the title A product as a foam, TLC R$_f$=0.29 (ethyl acetate:hexane:methanol:acetic acid, 10:4:2:0.2).

b)

(S)-1-[N-[3,3,3-Trifluoro-2-(mercaptomethyl)-1-oxo-propyl]-L-alanyl]-L-proline

The title A product (1.2 g., 3.12 mmol) under argon at 0° C. was treated with ammonium hydroxide (7 mL of 5M solution, prepared by diluting concentrated ammonium hydroxide with degassed water). After 10 minutes, the reaction was quenched with 10% potassium bisulfate (50 mL). The mixture was extracted with ethyl acetate and the organic fraction was washed with water and brine, dried (MgSO$_4$), and concentrated in vacuo to give 1.0 g. of a solid. Flash chromatography on silica gel (200 mL) and elution with ethyl acetate:hexane:methanol:acetic acid (10:6:2:0.2) gave the product as a foam. Trituration with hexane (containing a few percent ethyl acetate) afforded 750 mg. of the title (S) isomer product, m.p. 100°–110° C., TLC R$_f$=0.37 (ethyl acetate:hexane: methanol:acetic acid, 10:6:2:0.2), [α]$_D$=−65.8° (c=0.8, methanol).

Analysis calc'd. for C$_{12}$H$_{17}$F$_3$N$_2$O$_4$S·0.25 H$_2$O: C, 41.53; H, 5.09; N, 8.07; F, 16.42; S, 9.24; SH, 9.53 Found: C, 41.75; H, 4.87; N, 7.85; F, 16.41; S, 9.24; SH, 11.92.

(R)-1-[N-[3,3,3-Trifluoro-2-(mercaptomethyl)-1-oxo-propyl]-L-alanyl]-L-proline a)

(R)-1-[N-[3,3,3-Trifluoro-2-[(acetylthio)methyl]-1-oxo-propyl]-L-alanyl]-L-proline The ephedrine salt product of Example 54(a) (1.66 g., 4.35 mmol) was converted to the free acid and then to the acid chloride and reacted with a solution of L-alanyl-L-proline/bis(trimethylsilyl)trifluoroacetamide in acetonitrile as set forth in Example 59(a) to give 1.2 g. of the title A product as a foam, TLC $R_f$=0.37 (ethyl acetate:hexane: methanol:acetic acid, 12:6:2:0.2).

b) (R)-1-[N-[3,3,3-Trifluoro-2-(mercaptomethyl)-1-oxo-propyl]-L-alanyl]-L-proline The title A product (1.25 g., 3.25 mmol) was treated with ammonium hydroxide according to the procedure of Example 59(b) to yield after chromatographic purification and trituration with hexane (containing a few percent of ethyl acetate) 740 mg. of the (R) isomer title product, m.p. 100°–105° C., TLC $R_f$=0.37 (ethyl acetate: hexane:methanol:acetic acid, 12:6:2:0.2), $[\alpha]_D$= −124.2° (c=1.1, methanol).

Analysis calc'd. for $C_{12}H_{17}F_3N_2O_4S \cdot 0.25 \ H_2O$: C, 41.53; H, 5.09; N, 8.07; F, 16.42; S, 9.25; SH, 9.53. Found: C, 41.75; H, 4.95; N, 8.01; F, 16.59; S, 9.36; SH, 11.01.

EXAMPLE 61

(R,S)-α-[[3,3,3-Trifluoro-2-(mercaptomethyl)-1-oxo-propyl]amino]-1 H-indazole-3-propanoic acid a) 3-Methyl-1 H-indazole Concentrated HCl (23 mL) was added to neat 2-aminoacetophenone (11.3 g., 84 mmol) at −10° C. The resulting thick suspension was stirred rapidly while warming to −5° C. Sodium nitrite (5.8 g., 84 mmol) was added dropwise over 15 minutes as a solution in 13 mL of water while maintaining the temperature between −5° C. and 3° C. The reaction mixture was stirred an additional 15 minutes at 0° C., during which time it became an orange solution. At this time, the reaction was poured into a solution of sodium sulfite and sodium bisulfate at 5° C. [solution was made by dissolving sodium sulfite (21.12 g., 160 mmol) in a minimal amount of water (about 75 mL) and adding sodium bisulfate until no more dissolved. A small amount of water was added to dissolve any remaining solids]. The resulting yellow solution was allowed to stir for 15 minutes after which time a solid precipitated. The suspension was allowed to stand at room temperature overnight during which time the precipitate was replaced by a red oil floating on top of the aqueous layer. The entire mixture was basified with 1N sodium hydroxide and extracted with ethyl ether. The organic layer was washed with brine, dried (MgSO4), decolorized, and concentrated to a light yellow solid which was recrystallized from ethyl ether/pentane to afford 3.83 g. of the title A product as a tan crystalline solid, m.p. 110°–113° C.

b) 3-Methyl-1 H-indazole-1-sulfinic acid, phenyl ester

Benzenesulfonyl chloride (4.2 mL, 33 mmol) was added to a suspension of the title A product (3.5 g., 26.5 mmol) and powdered potassium hydroxide (7.5 g., 133 mmol) in dimethoxyethane (110 mL) at 0° C. The reaction mixture was warmed to room temperature and stirred for one hour. At this time, the reaction was poured into toluene (850 mL) and the resulting suspension was filtered through Celite. The filtrate was washed with brine, dried (MgSO4), and concentrated to a solid which was recrystallized from ethyl acetate/hexane to afford 5.6 g. of the title B product as a colorless crystalline solid, m.p. 141°–143° C.

c) 3-(Bromomethyl)-1 H-indazole-1-sulfinic acid, phenyl ester

A mixture of the title B product (3 g., 11 mmol), N-bromosuccinimide (1.95 g., 11 mmol) and benzoyl peroxide (12 mg.) in carbon tetrachloride (160 mL) was refluxed for 7 hours. After cooling to room temperature, the reaction mixture was filtered through Celite and the filtrate was concentrated to an orange solid. This solid was chromatographed on a 5×20 cm silica gel column using hexane:ethyl acetate (95:5) as the mobile phase. All the product containing fractions were concentrated to a solid which was recrystallized from ethyl acetate/hexane to afford 2.46 g. of the title C product as a colorless crystalline solid.

d) [3aS-[3aα,6α,7β]]-1-[2-[[Bis(methylthio)methylene]amino]-1-oxo-3-[1-(phenoxysulfinyl)-1 H-indazol-3-yl]propyl]-3 H-3a,6-methano-2,1-benzisothiazole,2,2-dioxide A solution of [3aS-[3aα,6α,7β-1-[[[bis(methylthio)methylene]amino]acetyl]hexahydro-3 H-3a,6-methano-2,1-benzisothiazole,2,2-dioxide [1.13 g., 3 mmol, prepared as described in Example 57(c)]in tetrahydrofuran (4.5 mL) was added dropwise to a solution of n-butyllithium (1.13 mL of 2.5M in hexanes, 2.82 mmol) in tetrahydrofuran (7.5 mL) at −78° C. After stirring for one hour at −78° C., the title C product (1.29 g., 2.82 mmol) was added dropwise as a solution in tetrahydrofuran (1.5 mL) and hexamethylphosphoric triamide (1.5 mL). Tetrabutylammonium iodide (spatula tip) was then added and the reaction mixture was stirred from −78° C. to 0° C. over 2 hours. The reaction was partitioned between water (250 mL) and ethyl acetate (250 mL). The organic layer was washed with water (2×100 mL) and brine (100 mL), dried (MgSO4), and concentrated. The residue was chromatographed on a 5×20 cm column eluting with 2 L hexane:ethyl acetate (8:2) and 2L hexane:ethyl acetate (7:3). The pure fractions were concentrated to afford 1.58 g. of the title D product as a colorless oil.

e) [3aS-[3aα,6α,7β]]-1-[2-Amino-1-oxo-3-[1-(phenoxysulfinyl)-1 H-indazol-3-yl]propyl]-3 H-3a,6-methano-2,1-benzisothiazole,2,2-dioxide A mixture of the title D product (1.53 g., 2.25 mmol) in 0.5N HCl (15 mL) was heated to 50° C., for 20 hours. After this time, the mixture was basified to pH 12 with 1N sodium hydroxide and the resulting basic layer was extracted with ethyl acetate (100 mL). The organic layer was washed with brine, dried (Na2SO4), and concentrated to a solid which was recrystallized from ethyl acetate/ hexane to afford 1.19 g. of the title E product as a colorless crystalline solid, m.p. 187°–188° C.

f) (S)-α-Amino-1 H-indazole-3-propanoic acid, hydrochloride

A mixture of the title E product (1.14 g., 2.1 mmol), lithium hydroxide hydrate (550 mg., 12.5 mmol), water (12.5 mL) and tetrahydrofuran (12.5 mL) was stirred for 96 hours at room temperature. A second portion of lithium hydroxide (100 mg., 2.5 mmol) was added as a solution in 3 mL of water. After an additional 18 hours, the reaction was diluted with water (50 mL) and the aqueous mixture was extracted with methylene chloride (2×30 mL) The aqueous layer was then acidified to pH 1.5 with 1N HCl and extracted with ethyl acetate (50 mL). The aqueous layer was then poured onto an HP-20 column (5×10 cm) which was eluted as follows: 400 mL of water; 200 mL of water: methanol, 9:1; 200 mL of water:methanol, 8:2; 200 mL water: methanol, 7.3; 200 mL water:methanol, 6:4; 200 mL water:methanol, 5:5. The pure fractions were concentrated to approximately 10 mL and the pH was readjusted to 1.5 with 1N HCl. This solution was concentrated to dryness and was coevaporated from methanol, ethyl acetate, and hexane. The resulting solid was stirred as a suspension in ethyl acetate for 24 hours, after which time it was filtered and washed with hexane. Drying afforded 598 mg. of the title F compound as an amorphous solid, $[\alpha]_D = +21.4°$ (c=0.44, methanol).

g)
(R,S)-α-[[3,3,3-Trifluoro-2-[(acetylthio)methyl]-1-oxopropyl]amino]-1-indazole-3-propanoic acid The ephedrine salt product of Example 54(a) (265 mg., 0.76 mmol) was partitioned between ethyl ether (60 mL) and dilute HCl (0.76 mL of 1N HCl in 60 mL of water). The ether layer was washed with water (2×60 mL), dried (MgSO$_4$), and concentrated. The residue was coevaporated from methylene chloride (2×10 mL). The free acid was then dissolved in methylene chloride (2 mL) and oxalyl chloride (0.066 mL, 0.76 mmol) was added. Dimethylformamide (5 μL) was added and the mixture was stirred at room temperature for 2 hours. Concurrently, bis(trimethylsilyl)trifluoroacetamide (0.64 mL, 2.27 mmol) was added to a suspension of the title F compound (150 mg., 0.54 mmol) in acetonitrile (2 mL). While stirring for 2.5 hours, this suspension became a light yellow cloudy solution. This mixture was cooled to 0° C. and the solution of the above acid chloride was added in one portion. The mixture was allowed to warm to 10° C. over 2 hours. 1N HCl (2 mL) were added and the reaction mixture was partitioned between ethyl acetate (75 mL) and water (75 mL). The ethyl acetate layer was then washed with brine (75 mL). The organic layer was dried (MgSO$_4$), concentrated, and coevaporated from toluene (3×15 mL). The residue was chromatographed on a 2.5×20 cm silica gel column using 1 L ethyl acetate:heptane: acetic acid (80:20:2) and 1L ethyl acetate:acetic acid (98:2) as the mobile phase. The pure fractions were concentrated to afford 127 mg. of the (R,S) isomer title G product as a white solid, m.p. 198°–204° (dec.).

h)
(R,S)-α-[[3,3,3-Trifluoro-2-(mercaptomethyl)-1-oxopropyl]amino]-1 H-indazole-3-propanoic acid Concentrated ammonium hydroxide (0.6 mL) was added to a suspension of the (R,S) isomer title G product (120 mg., 0.3 mmol) in deoxygenated water (2.4 mL). The resulting suspension was stirred for 2.5 minutes, after which time the reaction mixture was acidified with saturated potassium bisulfate solution to a pH under 2. The acidic layer was extracted with ethyl acetate (50 mL) and the ethyl acetate layer was washed with brine. The organic layer was dried (Na$_2$SO$_4$), concentrated, and preabsorbed on Celite. Chromatography on a 2.5×10 cm silica gel column using ethyl acetate: heptane:acetic acid, 75:25:2 as the mobile phase gave a solid residue which was coevaporated several times from heptane to afford 78 mg of the (R,S) isomer title product as a white amorphous solid, m.p. 218°–220° C., TLC R$_f$=0.17 (8:2, ethyl acetate: hexane +2% acetic acid), $[\alpha]_D = -15.5°$ (c=0.11, methanol).

Analysis Calc'd. for C$_{14}$H$_{14}$F$_3$N$_3$O$_3$S·0.2 H$_2$O: C, 47.09; H, 4.30; N, 11.21; F, 15.20; S, 8.55; SH, 8.82 Found: C, 47.10; H, 4.02; N, 10.85; F, 15.39; S, 8.20; SH, 10.11.

EXAMPLE 62

(S,S)-α-[[3,3,3-Trifluoro-2-(mercaptomethyl)-1-oxopropyl]amino]-1H-indazole-3-propanoic acid a)
(S,S)-α-[[3,3,3-Trifluoro-2-[(acetylthio)methyl]-1-oxopropyl]amino]-1 H-indazole-3-propanoic acid Following the procedure of Example 61(g) but employing the acid chloride obtained from the ephedrine salt product of Example 53(b), one obtains the (S,S) isomer title A product.

b)
(S,S)-α-[[3,3,3-Trifluoro-2-(mercaptomethyl)-1-oxopropyl]amino]-1 H-indazole-3-propanoic acid Treating the title A product with concentrated ammonium hydroxide according to the procedure of Example 61(h), one obtains the (S,S) isomer title product.

EXAMPLE 63

(αS)-α-[[3,3,3-Trifluoro-2-(mercaptomethyl)-1-oxopropyl]amino]-1 H-tetrazole-5-propanoic acid a)
(2S)-[[(Phenylmethoxy)carbonyl]amino]-3cyanopropanoic acid Bis (trimethylsilyl)trifluoroacetamide (9.4 mL, 35 mmol.) was added to a suspension of (αS)-amino-3-cyanopropanoic acid (2.0 g., 17.5 mmol.) in 10 mL of dry acetonitrile and the reaction mixture was stirred for 3 hours. Benzylchloroformate (2.5 mL, 17.5 mmol) was added, the reaction mixture was stirred overnight, concentrated in vacuo, and dissolved in ethyl acetate (200 mL). The organic solution was washed with water (2 x) and brine, dried (Na$_2$SO$_4$), and concentrated in vacuo. Crystallization from isopropyl ether yielded 3.82 g. of the title A product.

b)
(2S)-[[(Phenylmethoxy)carbonyl]amino]-3-cyanopropanoic acid, 1,1-dimethylethyl ester To a solution of the title A product (3.42 g., 13.8 mmol) and t-butanol (5.2 g., 70 mmol) in dry methylene chloride (20 mL), was added ethyl-3-(3dimethylamino)-propyl carbodiimide, hydrochloride salt (2.64 g., 13.8 mmol) and dimethylaminopyridine (0.2 g.). The reaction mixture was stirred overnight, diluted with methylene chloride (100 mL) and washed with 0.5 M HCl, saturated aqueous sodium bicarbonate, and brine, dried (Na$_2$SO$_4$), and concentrated in vacuo. The crude product was purified by chromatography through silica gel (100 g.) using a 1:1 ethyl acetate:hexane solvent system. The appropriate fractions were combined and concentrated to yield 2.3 g. of the title B product.

c) (αS)-α-[[(Phenylmethoxy)carbonyl]amino]-1 H-tetrazole-5-propanoic acid, 1,1-dimethylethyl ester The title B product (2.0 g., 6.57 mmol) and tri-n-butyltin azide (2.7 g., 8.0 mmol) were heated at 135° C. in xylene (30 mL) overnight. The reaction mixture was concentrated in vacuo, dissolved in 50 mL of 1:1:8 methanol:acetic acid:chloroform and stirred with 20 g. of silica gel overnight. The reaction mixture was concentrated in vacuo, placed on top of a 100 g. silica gel column and chromatographed with 3:3:96 methanol:acetic acid: chloroform solvent system. The appropriate fractions were combined and concentrated to yield 1.45 g. of the title C product.

d) (αS)-α-Amino-1 H-tetrazole-5-propanoic acid, 1,1-dimethylethyl ester

The title C (1.45 g.) product in methanol (40 mL) was hydrogenated overnight using 0.1 g. of 20% palladium hydroxide on carbon catalyst. The reaction mixture was filtered through Celite and the pad was washed thoroughly with methanol-water. The filtrate was concentrated in vacuo to yield 0.79 g. of the title D product.

e)
(αS)-α-[[3,3,3-Trifluoro-2-[(acetylthio)methyl]-1-oxopropyl]amino]-1 H-tetrazole-5-propanoic acid, 1,1-dimethylethyl ester The title D product (0.78 g., 3.67 mmol) was suspended in dry acetonitrile (8 mL). Bis(trimethylsilyl)trifluoroacetamide (1.87g., 7.34 mmol) was added at 5° C. and stirred for one hour at which point a clear solution was obtained. 2-Trifluoromethyl-3-acetylthiopropionic acid chloride (0.86 g., 3.67 mmol) was added at 0° C. and the reaction was stirred for 2 hours, diluted with ethyl acetate (150 mL), and the resulting solution was washed with water (2 x) and brine, dried ($Na_2SO_4$), and concentrated in vacuo. Crystallization from isopropyl ether yielded 0.95 g. of the title E product as a 1:1 mixture of isomers, m.p. 150°–158° C.

f)
(α,S)-α-[[3,3,3-Trifluoro-2-[(acetylthio)methyl]-1-oxopropyl]amino]-1 H-tetrazole-5-propanoic acid The title E product (0.9 g., 2.2 mmol) and anisole (0.1 g.) were dissolved in acetonitrile (5 mL). Trifluoroacetic acid (4 mL) was added and the reaction mixture was stirred overnight. The reaction mixture was concentrated in vacuo and chromatographed through 50 g. of silica gel using a 7:5:88 methanol:acetic acid:chloroform solvent system. The appropriate fractions were combined and concentrated to yield 0.68 g. of the title F product as a 1:1 mixture of isomers.

g)
(αS)-α-[[3,3,3-Trifluoro-2-(mercaptomethyl)-1-oxopropyl]amino]-1 H-tetrazole-5-propanoic acid A suspension of the title F product (0.4 g., 1.12 mmol) in concentrated ammonium hydroxide (0.72 mL) and water (1.6 mL) was stirred at room temperature under argon for 15 minutes. The resulting yellowish green solution was acidified with 5% potassium bisulfate to pH 1.5 and extracted with ethyl acetate (4×50 mL). The combined ethyl acetate extract was washed with water and brine, dried ($MgSO_4$), and evaporated under reduced pressure to give 0.29 g. of a light yelow gummy solid. Flash chromatography on 60 g. of silica gel using methylene chloride:methanol: acetic acid (15:1:1) as the eluent gave 0.24 g. of slightly yellow sticky solid which on trituration with hexane containing a few drops of methylene chloride, ethyl acetate, and methanol afforded 0.17 g. of the product. This product on further purification by preparative chromatography and trituration with hexane:ethyl acetate gave 0.07 g. of the title product as a white solid, m.p. 158°–161° C., TLC $R_f$=0.26 (methylene chloride: methanol:acetic acid, 10:1:1), $[\alpha]_D$=4.4° (c=0.5, methanol).

Analysis calc'd. for $C_8H_{10}F_3N_5O_3S$·0.08 hexane: C, 31.81; H, 3.50; N, 21.88; F, 17.80; S, 10.01; SH, 10.56 Found: C, 31.39; H, 3.37; N, 21.35; F, 18.27; S, 10.51; SH, 11.01.

EXAMPLES 64–83

Using the methodology outlined above, the following additional compounds can be prepared.

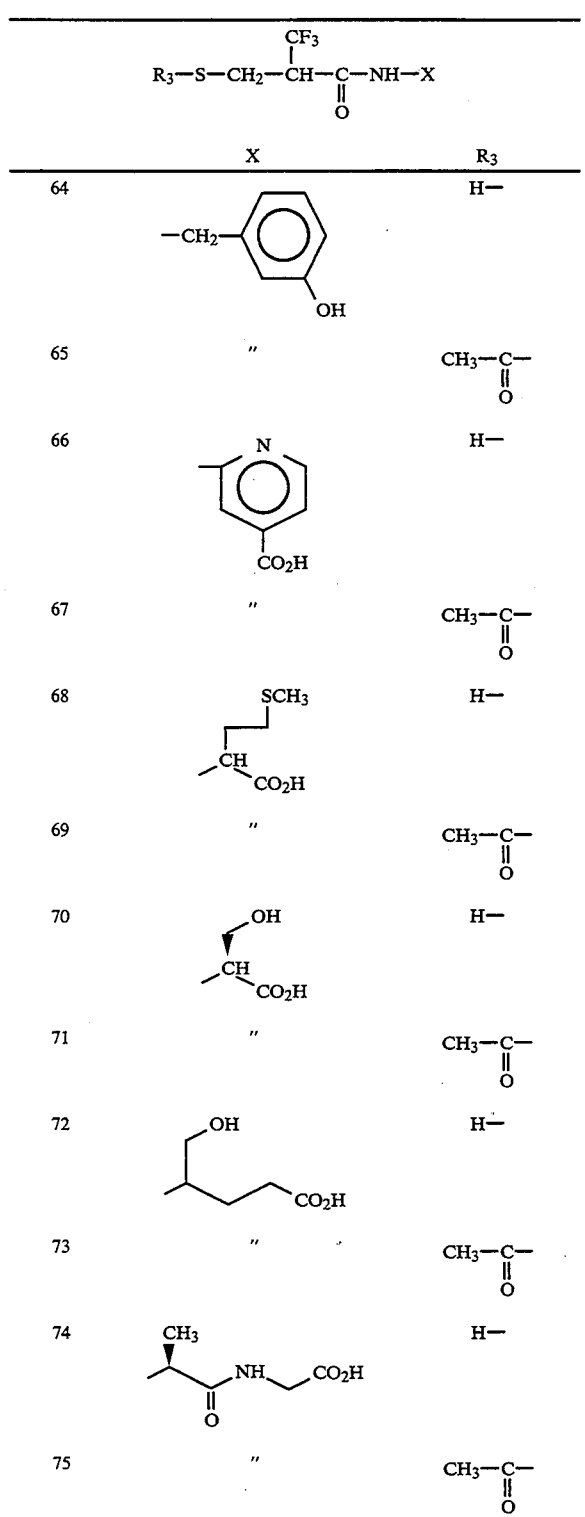

-continued

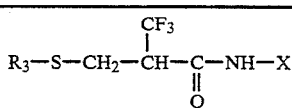

| | X | R₃ |
|---|---|---|
| 76 | —(CH₂)₃—CO₂H | H— |
| 77 | " | CH₃—C(=O)— |
| 78 | (2-pyrrolyl-CH(CO₂H)-) | H— |
| 79 | " | CH₃—C(=O)— |
| 80 | (2-(CH₃CH(C=O)NH-CH₂-)phenyl with CO₂H (L)) | H— |
| 81 | " | CH₃—C(=O)— |
| 82 | (phenyl-CH(CH₃)-C(=O)-NH-CH(iPr)-CO₂H) | H— |
| 83 | " | CH₃—C(=O)— |

EXAMPLE 84

1000 tablets each containing the following ingredients:

| | |
|---|---|
| N-[[3,3,3-Trifluoro-2-(mercaptomethyl)-1-oxopropyl]-L-tryptophan, isomer A | 100 mg. |
| Cornstarch | 50 mg. |
| Gelatin | 7.5 mg. |
| Avicel(microcrystalline cellulose) | 25 mg. |
| Magnesium stearate | 2.5 mg. |
| | 185 mg. | are prepared from sufficient bulk quantities by mixing the product of Example 9 and cornstarch with an aqueous solution of the gelatin. The mixture is then dried and ground to a powder. The Avicel and then the magnesium stearate are admixed with granulation. This mixture is then compressed in a tablet press to form 1000 tablets each containing 100 mg. of active ingredient. This same procedure can be employed to prepare tablets containing 50 mg. of active ingredient. Similarly, tablets containing 50 mg. or 100 mg. of the product of any of Examples 1 to 8 or 10 to 83 can be prepared.

EXAMPLE 85

Two piece #1 gelatin capsules are filled with a mixture of the following ingredients:

| | |
|---|---|
| N-[3,3,3-Trifluoro-2-(mercaptomethyl)-1-oxopropyl]-L-leucine, isomer B | 100 mg. |
| Magnesium stearate | 7 mg. |
| Lactose | 193 mg. |
| | 300 mg. |

In a similar manner, capsules containing 100 mg. of the product of Examples 1 to 20 and 22 to 83 can be prepared.

What is claimed is:

1. A compound of the formula $$R_3-S-CH_2-CH(-(CH_2)_n-CF_3)-C(=O)-NH-X$$

wherein X is

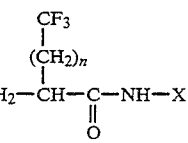

(L)

n is zero, 1 or 2;

R₁ is hydrogen, lower alkyl, halo substituted lower alkyl,

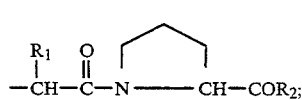

, —(CH₂)ᵣ—COR₉,

—(CH₂)ᵣ-cycloalkyl, —(CH₂)ᵣ-(α-napthyl),

—(CH₂)ᵣ-(β-naphthyl), 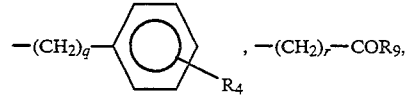

—(CH₂)ᵣ—NH₂, —(CH₂)ᵣ—SH, —(CH₂)ᵣ—S-lower alkyl,

—(CH₂)ᵣ—OH, 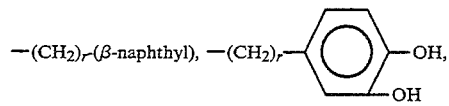

—(CH₂)ᵣ—O-lower alkyl,

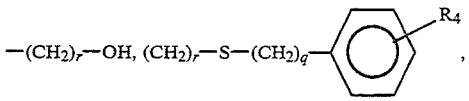 or

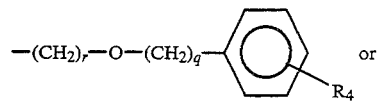

$R_2$ and $R_9$ are independently hydroxy, lower alkoxy, (phenyl)lower alkoxy,

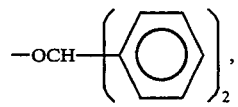

$-O^-M^+$ where $M^+$ is a salt forming metal ion,

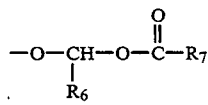

or $-NRR'$;

R and R' are independently hydrogen, alkyl or

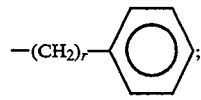

$R_3$ is hydrogen or

$R_4$ is hydrogen, lower alkyl of 1 to 4 carbons, lower alkoxy of 1 to 4 carbons, lower alkylthio of 1 to 4 carbons, halo, hydroxy, $CF_3$, phenyl,

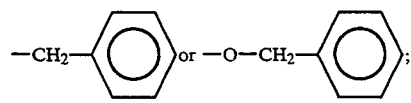

$R_5$ is lower alkyl

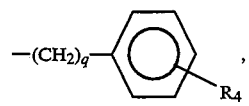

—$(CH_2)_q$-($\alpha$-naphthyl), —$(CH_2)_q$-($\beta$-naphthyl), or —$(CH_2)_q$-cycloalkyl;

$R_6$ is hydrogen, lower alkyl, cycloalkyl or phenyl;
$R_7$ is hydrogen, lower alkyl, lower alkoxy or phenyl;
r is an integer from 1 to 4; and
q is zero or an interger from 1 to 7.

2. A compound of claim 1 wherein
$R_3$ is hydrogen or

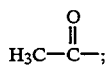

n is zero; and
X is

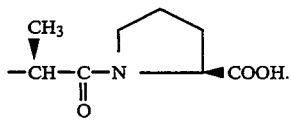

3. A pharmaceutical composition useful for reducing blood pressure and producing diuresis and natriuresis as well as treating congestive heart failure, renal failure, or hepatic cirrhosis comprising a pharmaceutically acceptable carrier and an effective amount of an endopeptidase inhibiting compound of the formula

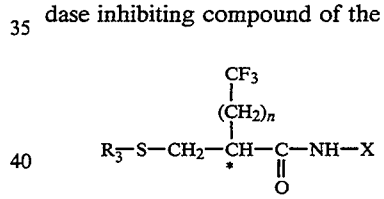

wherein X, n and $R_3$ are as defined in claim 1.

4. The compound of claim 2, (S)-1-[N-3,3,3-trifluoro-2-(mercaptomethyl)-1-oxopropyl]-L-alanyl]-L-proline.

5. The compound of claim 2, (R)-1-[N-[3,3,3-trifluoro-2-(mercaptomethyl)-1-oxopropyl]-L-alanyl]-L-proline.

* * * * *